(12) United States Patent
Sarcinelli et al.

(10) Patent No.: US 11,883,193 B2
(45) Date of Patent: Jan. 30, 2024

(54) PROCESS AND DEVICES FOR ACTIVATING A DRUG MEASURING DEVICE, ESPECIALLY AN ALCOHOL MEASURING DEVICE

(71) Applicant: Dräger Safety AG & Co. KGaA, Lübeck (DE)

(72) Inventors: Alexander Sarcinelli, Lübeck (DE); Michael Richenberger, Lübeck (DE); Carlo Rattey, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 500 days.

(21) Appl. No.: 17/082,763

(22) Filed: Oct. 28, 2020

(65) Prior Publication Data
US 2021/0128060 A1 May 6, 2021

(30) Foreign Application Priority Data
Nov. 4, 2019 (DE) ...................... 10 2019 007 620.6

(51) Int. Cl.
*A61B 5/00* (2006.01)
*A61B 5/18* (2006.01)
(Continued)

(52) U.S. Cl.
CPC .......... *A61B 5/4845* (2013.01); *A61B 5/0004* (2013.01); *A61B 5/0015* (2013.01);
(Continued)

(58) Field of Classification Search
CPC ... A61B 5/4845; A61B 5/0004; A61B 5/0015; A61B 5/18; A61B 5/742; A61B 5/7475;
(Continued)

(56) References Cited

U.S. PATENT DOCUMENTS 7,103,454 B2   9/2006  Stock et al.
7,945,076 B2   5/2011  Delean
(Continued)

FOREIGN PATENT DOCUMENTS

DE    102013018663 A1   5/2015
WO       2019111044 A1   6/2019
WO    WO-2019111044 A1 *  6/2019  ........... A61B 5/0017

*Primary Examiner* — Edward F Urban
*Assistant Examiner* — Wassim Mahrouka
(74) *Attorney, Agent, or Firm* — McGlew and Tuttle, P.C.

(57) ABSTRACT

A process and an activation device (30) provides a user (B) activation of a drug measuring device (100). This drug measuring device includes an input unit (3), a testing unit (6) for testing given samples and an image recording device (12). The activation device (30) receives an activation image set (InB), which was generated by the drug measuring device or by a drug measuring device and at least one image (40, 40.1) from the image recording device. The received activation image set is checked as to meeting a predefined release criterion. For this the activation image set is compared with a predefined reference image set (35) for the user. If the release criterion is met, the drug measuring device is released for the user. An activation data set (32) for the user is completed by at least one image of the activation image set, which shows the user.

14 Claims, 7 Drawing Sheets

(51) Int. Cl.
*G06V 40/16* (2022.01)
*G06V 40/50* (2022.01)
*A61B 10/00* (2006.01)

(52) U.S. Cl.
CPC ............... *A61B 5/18* (2013.01); *A61B 5/742* (2013.01); *A61B 5/7475* (2013.01); *G06V 40/172* (2022.01); *G06V 40/50* (2022.01); *A61B 2010/0009* (2013.01)

(58) Field of Classification Search
CPC ..... A61B 5/0022; A61B 5/082; A61B 5/1176; A61B 2010/0009; G06V 40/172; G06V 40/50; G06V 10/95; B60K 28/063
See application file for complete search history.

(56) References Cited

U.S. PATENT DOCUMENTS

| | | | |
|---|---|---|---|
| 8,240,419 B2 | 8/2012 | Zimmermann et al. | |
| 8,800,708 B2 | 8/2014 | Morley et al. | |
| 10,809,248 B2* | 10/2020 | Cado | G01N 33/4972 |
| 2008/0170762 A1* | 7/2008 | Endo | G01N 33/4972 |
| | | | 382/118 |
| 2009/0169068 A1* | 7/2009 | Okamoto | B60K 28/063 |
| | | | 382/118 |
| 2010/0108425 A1 | 5/2010 | Crespo et al. | |
| 2011/0292209 A1* | 12/2011 | Morley | B60K 28/063 |
| | | | 348/148 |
| 2015/0008063 A1 | 1/2015 | Walter et al. | |
| 2016/0153963 A1 | 6/2016 | Keays | |
| 2016/0161468 A1 | 6/2016 | Keays et al. | |
| 2017/0196504 A1 | 7/2017 | Kanukurthy et al. | |
| 2017/0249433 A1 | 8/2017 | Hagen et al. | |
| 2018/0313818 A1 | 11/2018 | Keays et al. | |

* cited by examiner

PROCESS AND DEVICES FOR ACTIVATING A DRUG MEASURING DEVICE, ESPECIALLY AN ALCOHOL MEASURING DEVICE

CROSS REFERENCE TO RELATED APPLICATIONS

This application claims the benefit of priority under 35 U.S.C. § 119 of German Application 10 2019 007 620.6, filed Nov. 4, 2019, the entire contents of which are incorporated herein by reference.

TECHNICAL FIELD

The present invention pertains to a process as well as to devices and systems for activating and using a drug measuring device, especially an alcohol measuring device.

TECHNICAL BACKGROUND

When a person consumes alcohol-containing beverages, gas is exchanged in their pulmonary alveoli between the inhaled air and the alcohol consumed. The inhaled fresh air therefore absorbs alcohol, and the air subsequently exhaled contains alcohol. An alcohol measuring device is capable of measuring the alcohol content in the exhaled air and thereby of determining the alcohol content in the blood—or of determining that the person tested is completely sober. Other drugs can be detected, for example, in the saliva of a person, for which a corresponding drug measuring device is used.

It is known that authorized persons, for example, police officers, conduct a traffic control and use at least one drug measuring device in this connection in order to test road users, especially to check whether tested automobile drivers are sober or not. Furthermore, it is known that a drug measuring device, especially an alcohol measuring device, may be installed in a motor vehicle. This drug measuring device only makes it possible to move the motor vehicle if it is positively determined that the automobile driver is drug-free, especially sober.

It is known, furthermore, that it is possible to monitor from a distance whether a human being is sober or not (Remote Alcohol Monitoring, RAM). Alcohol measuring devices for the RAM are known, for example, from US 2016/0161468 A1 and US 2016/0153963 A1 as well as from US 2018/0313818 A1.

US 2010/0108425 A1 describes an interlock system, which releases the ignition of a motor vehicle only if the person, who is sitting in the driver's seat, has been recognized as an "authorized operator" and if this person passes an "impairment test," especially if no alcohol is detected in the exhaled air. Biometric data of the person sitting in the driver's seat are detected in step 420 of FIG. 4 and compared with an entry in an interlock data bank. If the person sitting in the driver's seat is not recognized as an authorized person, a vehicle immobilizer is triggered. If the person is recognized as an authorized person (step 450), it is checked whether a "court-mandated impairment test" is to be carried out (step 460).

In US 2008/0170762 A1, a breath sample, which has been exhaled by a person, is tested for alcohol. In addition, a picture of that person is taken. This picture of the person, who has given the sample, is compared with a picture of a user, said photo of the user being stored in a data bank. It is checked thereby whether the user or another person is actually being tested for alcohol.

SUMMARY

A basic object of the present invention is to provide processes and devices for making it difficult to manipulate a drug measuring device during use of the drug measuring device, especially of an alcohol measuring device, during remote alcohol monitoring.

The present invention is accomplished by an activation process having features according to the invention, by an activation device having features according to the invention, by a drug-measuring system having features according to the invention, by a monitoring system having the features according to the invention and by a monitoring process having the features according to the invention. Advantageous embodiments are described. Advantageous embodiments of the activation process are also advantageous embodiments of the activation device, and advantageous embodiments of the monitoring system are also an advantageous embodiment of the monitoring process.

The drug measuring device, to which the processes and devices according to the present invention pertain, comprises
an input unit,
a testing unit and
an image recording device.

A person can give a user sample (a fluid sample), especially a breath sample or a saliva sample, from himself or herself by means of the input unit.

The testing unit is capable of detecting the result that the content of at least one predefined substance in a sample, which was given into the drug measuring device, is above a predefined limit. Or it is capable of ruling this result out. The testing unit is optionally capable of determining the content of the substance quantitatively. The substance or substances for which the testing unit shall test a given sample is/are predefined. The substance or a substance is especially alcohol, but it may also be another drug/narcotic. It is possible that the testing unit is capable of testing the sample for different substances and a respective limit each is predefined for each substance.

The image recording device is capable of generating at least one picture of a person who is using the input unit in order to give a sample, and it is preferably capable of taking a plurality of pictures one after another.

The activation process according to the present invention is carried out with the use of a data-processing activation device. The present invention pertains, furthermore, to such a data-processing activation device.

The activation device according to the present invention has read access at least at times and write access at least at times to an activation data bank. An activation data set for the user is stored in this activation data bank. This activation data set comprises a reference image set. The reference image set comprises at least one predefined reference image, preferably a plurality of reference images. The reference image or each reference image shows the face of the user.

An activation phase is carried out according to the present invention. This activation phase comprises the following steps:
The activation device receives an activation image set. This activation image set was generated by the drug measuring device and comprises at least one image, the image or each image of the activation image set having been generated by the image recording device of the drug measuring device to be released or by the image-recording device of another drug measuring device. The activation image set preferably comprises a plurality of images. It is possible that the images of the activation image set originate from the image recording devices of different drug measuring devices.

The activation device checks whether or not the received activation image set meets a predefined release criterion. This check comprises the step that an image comparison is carried out between the reference image set and at least one image of the received activation image set. Each image of the reference image set used for the image comparison shows the face of the user.

The activation device carries out this image comparison itself automatically. Or else it triggers the step that such an image comparison is carried out automatically or manually as well as at a distance in space from the drug measuring device, and it detects the result of the image comparison.

The activation device carries out the checking of whether or not the release criterion is met as follows: The checking only yields the result that the release criterion is met if at least one image of the received activation image set has been recognized according to the image comparison as an image that shows the face of the user.

If the release criterion is met, the activation device releases the drug measuring device for the user. It preferably changes the activation data set for the user correspondingly. If the release criterion is met, the activation device completes, in addition, the activation data set for the user by at least one image of the activation image set. The added image or each added image has been recognized as an image that shows the face of the user.

If the drug measuring device has been released for the user, it can be used by the user during a subsequent use phase. At least one drug test and preferably a plurality of drug tests one after another can be carried out for the user with the released drug measuring device during this subsequent use phase. It is checked during the drug test or during each drug test whether it is indeed the user or some other person who is giving the sample. At least one image, which is comprised by the activation data set for the user and shows the face of the user, and preferably at least two images from the activation data set are used for this checking. The released drug measuring device is preferably capable of transmitting a message on the result of a drug test to a receiver located at a distance in space.

As long as the drug measuring device has not yet been released for the user, the user cannot yet use it for a drug test and, in particular, the user cannot meet any condition or make any commitment with this drug measuring device, even if the user is already in possession of the drug measuring device. If the activation phase does not lead to a release of the drug measuring device for the user because the release criterion is not met, the user is also unable to perform a drug test with that device.

A drug measuring device is activated according to the present invention. The drug measuring device is released for a certain user during the activation phase—or it is not released. This user must or shall or wants to repeatedly give a sample each from himself or herself into the input unit of the drug measuring device during the subsequent use phase, and the testing device tests the given sample, i.e., it performs each time there is a drug test. The human being, who does actually give a sample, will hereinafter be called "the giving person." The "user" is the person who must or shall or wants to use the drug measuring device in order to be monitored, and to whom the activation phase pertains. The user shall be the giving person. However, a person other than the user could give a sample in order for the user to be able to hide a drug consumption. The two different terms "user" and "person" will therefore be used.

The processes and devices known from the state of the art require that a drug measuring device be already assigned to a certain user and that the at least one image or biometric data, which show this user, be stored in a central data bank. The processes and devices check whether a person, who gives a drug sample, is indeed the authorized user and/or another person, and/or whether this authorized person is under the influence of drugs or not. In particular, devices and processes for checking whether a user is allowed to put a motor vehicle into operation (interlock systems and interlock processes) are known from the state of the art. The devices and processes known from the state of the art require at least implicitly that a drug measuring device be already assigned to the user without it being specified how this should happen. The devices and processes consequently describe the use phase, and predefined reference images of the user are used during the use phase according to the state of the art. The gap, which happens prior to the use phase, is filled by the activation process according to the present invention and by the activation device according to the present invention.

According to the present invention, a drug measuring device is released, or also not released, for the user. A predefined reference image set with at least one reference image is used for this release check, and the reference image used or each reference image used shows the face of the user and originates, for example, from an official photo ID and/or had been prepared by an authorized person. The feature that a reference image set is predefined and used for the release check makes it possible for the user to register at the activation device from a remote location and to request from a remote location that a release check be carried out. It is possible but, thanks to the present invention, not necessary for the user to visit a issue center or a service center for a release check. This feature eliminates the need for the user to travel as well as the necessity to disclose himself or herself as a sentenced drug user to a person at the issue center/service center.

Furthermore, it is possible, but, thanks to the present invention, unnecessary to keep respective suitable drug measuring devices available in many issue centers or service centers or to have the technical equipment and the qualified staff available at an issue center/a service center for a release test. The user is not bound to the office hours of an issue center. The user can rather generate the images of the activation image set at any desired location as soon as the user is in possession of the drug measuring device to be released, or of another drug measuring device with an image recording device.

A user could be tempted to manipulate during the use phase while giving a sample in order to be able to consume a drug despite the sentence or commitment, for example, in one of the following ways:

A sample is given into the input unit by another person or, e.g., by a correspondingly trained pet or a robot rather than by the user, who has been ordered to give the samples or has committed himself or herself to give the samples into the input unit.

The user does not give a sample that originates from their body, especially no breath sample or saliva sample, but the user gives in another manner a gaseous or liquid object to be tested in the hope that the drug measuring device would incorrectly assume that object given for testing to be a sample from the body of the user and would test this sample for the drug. If this object to be tested is free from the substance, the testing unit will provide the negative result desired by the user.

The risk that the user will be successful with such an attempted manipulation is reduced thanks to the present invention, since images of the activation image set, which were taken by an image recording device of a drug measuring device and have "passed" the release test, can be used during the use phase.

On the other hand, the present invention diminishes the risk that an attempted manipulation is incorrectly assumed, even though the user gives a sample from himself or herself correctly. This may happen, for example, if a picture of the face of the user is generated while the sample is being given and is compared with a stored comparison image, but the appearance of the user has changed compared to the time at which the reference images had been taken. This may also happen when the comparison image was not taken by a drug measuring device and it therefore differs significantly from the image taken at the time when the sample is being given.

These two desired effects, namely that the risk of an attempted manipulation is reduced and that a false alarm is generated less often because of a supposed attempted manipulation, are generated especially by the fact that the present invention makes it possible for an image comparison carried out during the use phase to have the following features:

Images are transmitted and used according to the present invention both during the activation phase and during the subsequent use phase in order to check whether the samples have indeed been given by the user rather than by another person. The use of images reduces the risk that what the user gives is not a breath sample from himself or herself but something else compared to the mere checking of fingerprints or other biometric features. If only fingerprints were checked and compared, the user could provide their fingerprint but another person could give a sample. The use according to the present invention of images reduces this risk markedly. The present invention may also be used in combination with fingerprints.

An image comparison is carried out according to the present invention between the reference image set and the received activation image set during the activation phase. The comparison needs to be carried out not only with the reference image but with at least one image of the activation image set. It is possible to use for this image comparison only images of the activation image set that do indeed show the face of a person with a sufficient image quality and, in particular, it is possible not to use any reference image at all.

The activation data set is completed according to the present invention for the user by at least one image of the activation image set, which image shows the face of the user according to the image comparison and not that of another person or something else.

According to the present invention, an image comparison is carried out during the activation phase between the reference image set and at least one image of the received activation image set. This image comparison may be carried out at a distance in space from the drug measuring device, which makes it possible to make available for this image comparison a higher computing power than is usually available in a motor vehicle or in a portable device or in the home of a user. Since this image comparison is carried out once during the activation phase, the image comparison can be carried out automatically with a high-performance computer or manually by an authorized person. This reduces the risk of an incorrect result of the image comparison during the activation phase. Such an image comparison with a lower risk of an incorrect decision would not be possible or it would not at least be practical if a corresponding image comparison would have to be carried out at the time of each drug test during the use phase.

The image comparison during the use phase can be carried out between images that were generated during the activation phase by the drug measuring device and images that were generated during the use phase by the same drug measuring device or by another similar drug measuring device. It is possible thereby to rule out the risk of an error that could result from the fact that significantly different image recording devices are used during the activation phase and during the use phase, for example, the image recording device of a Smartphone or a special digital camera and the image recording device of the drug measuring device during the use phase only.

It is made easier, even during the activation phase, to use only images for the image comparison that show a person during the giving of a sample into the input unit. As a rule, such an image shows a part of the input unit. It is possible to allow only such images during the activation phase.

It is made possible to use different images of the user for the image comparison, these images having been transmitted as parts of the activation image set and these images showing the user under different light conditions and/or from different viewing directions.

The present invention makes it possible for the user to use the drug measuring device released for them during the subsequent use phase and to give a sample from himself or herself repeatedly into the drug measuring device according to the predefined conditions of a sentence or commitment. In order to avoid an attempted manipulation, at least one picture of the giving person is generated during the use phase and is compared with at least one image and preferably with a plurality of images, said image or each image used for the comparison belonging to an activation data set for the user and being stored in a central use data bank. The present invention makes it possible to use for this comparison at least one image of the activation data set, which was added to the activation data set during the activation phase. This image may have a sufficient image quality and show the face of the user completely, while the user is giving a sample. This image was likewise generated by the drug measuring device to be released or by another drug measuring device. Since at least one such image can be used for the comparison, the risk that a person other than the user gives a sample undetected, on the one hand, and, on the other hand, the risk that the user gives from himself or herself something else rather than a correct sample is reduced, because the user must have a greater distance to the input unit for doing so than in case of giving a sample correctly.

More time is frequently available during the activation phase for an image comparison, especially for a manual image comparison by an authorized person, than during the use phase. The images added during the activation phase therefore often show the face of the user with a higher image quality than does a predefined reference image, and the image comparison during the subsequent use phase will lead to a correct result with a higher level of certainty. In addition, the images are generated by drug measuring devices, in one configuration always by the same drug measuring device, during both the activation phase and the use phase. It becomes possible that an authorized person will perform the image comparison manually (visually) or check visually the result of an image comparison carried out automatically during the activation phase. Such a manual image comparison or a manual checking of a comparison carried out automatically would not, as a rule, be practical during the use phase.

The activation process according to the present invention is carried out with the use of an activation device. This activation device according to the present invention is preferably arranged at a distance in space from the drug measuring device to be released and is thereby better protected from a possible manipulation by the user. The activation device preferably carries out an activation phase each for a plurality of drug measuring devices, as a rule, for different users. As a result, it can have a higher computing capacity and/or higher storage capacity.

The present invention makes it possible for the drug measuring device to transmit images of the face of the user again during the use phase, and these images are preferably compared with at least one reference image and/or with at least one image transmitted as a part of the activation image set. This leads to a higher level of certainty in avoiding a false alarm, which could otherwise occur if the appearance of the user changes in the course of the use phase, for example, because hair grows or falls out or the user now has a beard or wears eyeglasses or has no beard or eyeglasses any more or a scar appears or disappears again on the face of the user during the use phase. The risk that the user makes an attempted manipulation on this occasion and transmits images of another person during the use phase can be reduced.

In case the sample is given correctly, each image, which is generated of the person giving the sample during the use phase, inherently shows, as a rule, at least a part of the drug measuring device, especially the input unit. It is possible that the image or each image used for the comparison in the use data set for the user likewise shows this part of the drug measuring device in addition to the face of the user, this part being a part of the same drug measuring device or at least of a similar drug measuring device. A predefined reference image shows, as a rule, no drug measuring device.

The risk that this image comparison yields an incorrect result during the use phase would be much greater if only the reference image or a predefined reference image, which does not, as a rule, show an input unit of a drug measuring device, were exclusively used during the use phase as well. Consequently, the present invention reduces the risk that an image comparison during the use phase yields an incorrect result, especially that the giving person is wrongly not recognized as the user.

An activation data set for the user is stored according to the present invention in the activation data bank. This activation data set comprises a reference image set with at least one predefined reference image. The reference image or each predefined reference image shows the face of the user. The reference image belongs, e.g., to an official personal document (identity card or passport or driver's license) or is a part of an official document on the user or was taken by an authorized person. The reference images are not necessarily generated with the image recording device of the drug measuring device and they do not necessarily show the input unit of the drug measuring device. It is possible to take the reference images in an environment and in a situation in which a manipulation is ruled out or is made at least very difficult. At least one reference image may meet an official specification on an image for a photo ID. As a rule, these specifications rule out the possibility that the image could show an input unit. During the generation of the reference images, the user does not necessarily need to carry the input unit of the drug measuring device with him, because the user would then have to disclose himself or herself as a potential drug user. In addition, the reference images can be prepared before the drug measuring device is made available to the user.

The process according to the present invention and the device according to the present invention consequently use two types of images:

On the one hand, the reference images, which can be prepared in a tamper-proof manner, show indeed the face of the user, but are not necessarily taken by means of the drug measuring device and not necessarily taken with the viewing directions and light conditions that occur during the activation phase and during the subsequent use phase, and on the other hand, the images of the activation image set, which are generated by the drug measuring device or by a drug measuring device, and therefore under the same or at least similar conditions as during the subsequent use phase, which do, however, possibly show a person other than the user; this deliberate manipulation or this error is, as a rule, detected by the image comparison according to the present invention.

An image comparison, during which at least one reference image is compared with at least one image, which was transmitted as a part of the activation image set, is carried out according to the present invention during the activation phase. In one configuration, the activation device—or a special image comparison device—carries out this image comparison automatically.

In another configuration, the activation device triggers the process that an authorized person carries out this image comparison. The activation device generates a comparison, which shows the reference image or a reference image as well as the image or an image of the activation image set. The authorized person can preferably change the view of an image, for example, allow a displayed image to rotate, to become enlarged or reduced by calculation. The authorized person enters the result of the image comparison. The activation device detects the inputted result.

This image comparison is preferably carried out remotely from the drug measuring device. Since the image comparison is carried out automatically by the activation device or by the special image comparison device or else manually (visually) by the authorized person, the risk that the result of this image comparison is manipulated with is reduced. In particular, it is made difficult for the user or another person to influence the performance or the result of the image comparison in an unauthorized manner.

In a first alternative, the activation device carries out the image comparison between the reference image set for the user and at least one image of the activation image set automatically. In a second alternative, the activation device triggers the image comparison and detects the result of the image comparison, i.e., it detects an input of an authorized person or an output of a special image comparison device, this input or output comprising the information of which image of the activation image set shows the face of the user and which does not. The person who enters the result of the image comparison preferably authorized himself or herself before by a usual authorization process. The image comparison is carried out at a distance in space from the activation device and at a distance in space from the drug measuring device in the first alternative and preferably also in the second alternative. The image comparison may be carried out automatically in this second alternative as well, e.g., by a separate image comparison device in this case, which may be responsible for a plurality of activation devices and may therefore have a large computing capacity. It is also possible that an authorized person carries out the image comparison manually (visually). The activation device triggers the step that an image of the activation device and a reference image are displayed on an output device, e.g., on the same screen or next to one another or vertically or obliquely one on top of another on two screens. An input, which is carried out by the authorized person, is detected and sent to the activation device.

The two possible configurations of the second alternative may also be combined with one another. The image comparison device compares the images automatically, and an authorized person checks the automatically obtained result of the image comparison and confirms or overrides this. The activation device decides on whether the release criterion is met or not depending on a detected input or on at least one detected input.

In a preferred configuration, the drug measuring device is made available to the user already before the activation phase, for example, it is given to them in person or is sent to them by mail. This configuration makes it easier to manufacture a plurality of drug measuring devices of the same type and then to carry out a respective activation phase for each drug measuring device for a user. The steps of the activation phase may be carried out at any desired location. It is made possible, in particular, that images are generated during the activation phase at the location or at least at a location at which the drug measuring device will be used during the subsequent use phase. This configuration reduces the risk that a picture of the giving person will be wrongly classified during the use phase as a picture not originating from the user because the ambient conditions during the activation phase and during the use phase differ significantly from one another. In particular, the images of the activation image set and the images that are generated during the subsequent use phase preferably originate from the same drug measuring device, which has already been made available to the user prior to the activation phase, or at least both originate from one drug measuring device.

The activation device is preferably positioned at a distance in space from the drug measuring device in this configuration. The release of the drug measuring device for the user triggers the step that a release message is transmitted to the drug measuring device. The drug measuring device then puts itself into a state or is put from the outside into a state in which it is capable of carrying out at least one drug test. For example, a password is sent to the user. This configuration reduces the risk that the user uses a drug measuring device that has not yet been released for a drug test.

In one configuration of this embodiment, the user picks up the drug measuring device at an issue center. The drug measuring device is then in the possession of the user, but it is not yet released for the user. In another configuration of this configuration, the activation data set comprises for the user a predefined mailing address. After the user has registered and at least one reference image of the user is available, the process of sending and/or transporting the drug measuring device to the predefined mailing address is triggered. The drug measuring device is preferably transported to the mailing address already before the activation phase. This other configuration eliminates the need to have to keep a suitable alcohol measuring device in stock at many issue centers. It is sufficient that a sufficient number of drug measuring devices are available in a central warehouse.

The activation phase is then carried out in both configurations, i.e., after the user has come into possession of the drug measuring device. As a result, the drug measuring device with the image recording device is available for generating the images of the activation image set. The same image recording device of the drug measuring device is preferably used during the activation phase and during the subsequent use phase, which reduces the risk of an incorrect result during an image comparison, compared to a possible configuration in which different image recording devices are used.

In another configuration, the activation phase is carried out first without the user being in possession of the drug measuring device intended for him, and the drug measuring device is then sent to the user, e.g., to the predefined mailing address, or is made available for being picked up in person when the activation device has released it for the user. The user goes to the location at which the drug measuring device is located, and the image recording device of the drug measuring device generates at that location the images of the activation image set. This configuration eliminates the need to have to return or to send back a drug measuring device after an unsuccessful release process. The user rather takes the drug measuring device with them when it is released for him. In addition, this configuration reduces the risk of manipulations and damage because the user is not yet in possession of the drug measuring device at the time of the activation.

In a variant of this configuration, the images of the activation image set are generated by the image recording device of a reference drug measuring device. The further steps of the activation phase pertain to a second drug measuring device, which is different from the reference drug measuring device and which is released for the user—or is not released. Each further drug measuring device and the reference drug measuring device may be similar devices or at least comprise similar image recording devices.

In this modified configuration, the drug measuring device that is released for the user after a successful activation phase does not necessarily have to be available at the location at which the images of the activation image set are generated. It is sufficient to provide at this location a reference drug measuring device, and this reference drug measuring device can be used to release different additional drug measuring devices one after another, even for different users. The activation image set is transmitted from the reference drug measuring device to the activation device. The images of the activation image set are also generated by the image recording device of a drug measuring device in this different configuration, preferably during the use is giving a sample, and not by an image recording device of another type.

The step in which a person is giving a sample from himself or herself may especially comprise the step that the person releases a breath sample into the input unit or gives a saliva sample into the input unit.

The drug measuring device can be configured such that a user of the drug measuring device can carry with them the complete device or at least a part with the input unit and the testing unit. The need for a user to go to a certain location to give a sample during the use phase is thus eliminated. The user can rather carry out the giving of a sample into the input unit at a location at which the user wishes to be. It is made possible to request the immediate giving of a sample from the user during the use phase without the user knowing the time at which this request will be made in advance, and the user can indeed give the requested sample immediately thanks to the mobile device. Thus, the user cannot argue that the user could not give a sample because no device was available. This configuration reduces the risk that the user ingests a drug undetected.

This preferred configuration with a mobile drug measuring device or mobile part is especially advantageous when the user is sentenced based on a court decision to give a sample from himself or herself into a drug measuring device repeatedly. As a result, it shall be checked whether the user is indeed sober, i.e., has not consumed alcohol and/or at least one other drug predefined for the testing; more precisely, it shall be checked whether or not the content of at least one predefined drug in the body of the user is below a predefined detection limit or another predefined limit. It is also possible that the user has committed himself or herself to undergo such a regular check. Thanks to the mobile drug measuring device, the user can comply with this court-ordered condition or commitment even if the user has to or wants to give a sample several times daily, e.g., at randomly predefined times, and can nevertheless pursue an occupation and/or leisure activities.

In a preferred embodiment, the activation device sorts out the images that do not meet a predefined quality criterion from the activation image set received before an image comparison. Examples of such sorted-out images are:

The image does not show completely the face of a person but only a part of the face.

The image does not show a person at all or it does not show the face of a person.

The image was taken under unsuitable light conditions and therefore has no sufficient contrast.

The image shows the face of a person with an excessively low resolution, for example, because the person was positioned too far from the image recording device or the image recording device had an incorrect setting or an unsuitable image recording device was used.

The image shows the face of a person in front of an unsuitable background, for example, in front of a window or of a light source (back-lighting) or in front of a high-contrast wall.

This feature that unsuitable images are sorted out reduces the number of image comparisons necessary during the activation phase. Nevertheless, a release of the drug measuring device is still possible, namely if the activation image set comprises a sufficient number of images, which meet the quality criterion and show the face of the user. In other words, the activation device identifies the images of the received activation image set that meet the predefined quality criterion, especially show the face of a person completely and/or have a sufficient image quality and/or were taken under suitable light conditions.

According to the present invention, the activation data set is completed by at least one image, which shows the face of the user. This image or each added image preferably meets the predefined quality criterion.

According to the present invention, the activation device checks whether or not the received activation image set meets a predefined released criterion. In one configuration, a minimum number N of transmitted images are predefined. The release criterion is only met if at least N images of the activation image set have been recognized as being images that show the face of the user. These N images preferably must meet the quality criterion. It is, of course, possible that the release criterion is not met even if at least N images originate from the user, for example, because the quality criterion is met by too few images.

An image of the person who is giving a sample into the input unit of the drug measuring device is likewise taken during the use phase. The giving person looks in a defined viewing direction relative to the image recording device during the image generation. This viewing direction may vary from one sample to the next, even if a defined viewing direction is predefined for the user.

It would often be undesirable to suspect an attempted manipulation or a violation of the court-ordered condition or the commitment merely because different viewing directions occur during different samples. A set of at least two different viewing directions of a person relative to the image recording device are therefore predefined in one configuration. The release criterion is predefined such that it is only met if the activation image set always comprises for each predefined viewing direction at least one image, preferably an image that meets the predefined quality criterion. The release criterion is preferably met if the images that have been recognized as showing the user do all show the user in all predefined, different viewing directions relative to the image recording device. These images must preferably meet the quality criterion. The configuration with at least two different viewing directions reduces the risk of a false alarm, which could otherwise occur if the user is always looking in a first direction relative to the image recording device during the taking of the images during the activation phase and is looking in another direction while giving a sample during the use phase.

In an alternative configuration, the release criterion is met if the images show the user under at least two different light conditions. This configuration takes into consideration the possibility that the user carries out drug tests one after another under different light conditions during the use phase, especially based on different seasons or if the drug measuring device is a mobile device and can therefore also be used during travels. The release criterion is preferably met only if the activation image set of the user comprises images of a sufficient quality under different light conditions, especially in each lighting situation of a predefined set of lighting situations. This configuration also reduces the risk of false alarms.

The two configurations with the viewing directions and with the light conditions can be combined, i.e., the activation image set must comprise images with different viewing directions and different light conditions, which preferably meet the quality criterion.

According to the present invention, the activation device carries out an image comparison between the reference image set for the user and at least one image of the received activation image set, preferably a comparison of the reference image set with each image of the activation image set, which image meets the quality criterion. In a preferred embodiment, the activation device—or a special image comparison device located at a distance in space—carries out during this image comparison at least one individual comparison between an image of the activation image set and a predefined reference image of the activation data set. During each individual comparison, it calculates a degree of agreement between these two images. If this degree of agreement is above a predefined limit, the activation device decides that the checked image of the activation image set does indeed show the user.

The activation device preferably carries out first a registration phase and then the activation phase according to the present invention. The registration phase comprises the following steps:

The activation device receives a registration message. This registration message comprises the reference image of the user or a predefined reference image of the user and optionally additional data on the user, e.g., a copy of a court-ordered sentence and/or a mailing address.

The activation device enters the activation data set for the user in the activation data bank, doing this such that this activation data set comprises the reference image set with the reference image or with each reference image that was transmitted as a part of the registration message.

The configuration with the registration phase makes it possible that the user will register himself or herself and trigger the activation from the distant location without having to visit a registration office.

It is possible that the user intentionally or unintentionally generates images not only of himself or herself but additionally also images of at least one other person, who is likewise giving, for example, a sample, during the activation phase. The activation image set may comprise in this case images of at least two persons. In one configuration, the activation device—or a special image comparison device located at a distant location—groups in one configuration at first the images of the activation image set by calculation. It preferably uses for this only the images that meet the predefined quality criterion. The activation device generates at least one group of images of the activation image set. All images of a group show the same person, and two images of two different groups always show different persons. It is possible that one group comprises the images that do not show the face of a person completely. If only a single group is generated during this grouping, all images of the activation image set—or at least those with a sufficient image quality—show the face of the same person, but not necessarily the face of the user. These images are then compared with the reference image set.

If, by contrast, at least two different groups have been generated during this grouping, the release process is interrupted in one configuration because an attempted manipulation is suspected. In another configuration, the activation device automatically selects a group and carries out image comparisons between the reference image set and the images of the selected group. The activation device uses the reference image set for the selection of a group. This selected group is compared with the reference image set. This configuration reduces the number of necessary image comparisons. It preferably selects the group that has the lowest degree of non-agreement with the reference image set. This configuration reduces the risk that the incorrect group will be selected.

In a preferred configuration, the activation device releases the drug measuring device for the user only if it was determined that at least one image shows the face of the user and it was determined, moreover, that this image shows the user while the user is giving a user sample into the input unit. The drug measuring device preferably generates a corresponding instruction and outputs this instruction in a form perceptible by a human being.

This configuration further reduces the risk that an image, which was generated in the subsequent use phase, is wrongly classified as an image that does not show the face of the user, because if the drug test is carried out correctly, each image generated by the image recording device shows during the use phase the face of a person, while this person is giving a user sample into the input unit. An image that shows the face of a person while this person is giving a user sample therefore shows, as a rule, at least partially the input unit and it therefore differs from an image that shows the face of the same person but not the input unit.

In one configuration, the activation device is located at a remote location in space from the drug measuring device. The same activation device for a plurality of drug measuring devices is preferably capable of carrying out the respective activation phase, and the activation data bank comprises activation data sets for a plurality of users with a respective reference image set for each. This configuration makes it easier to embody the activation device on a central data processing unit and to enable an authorized person in a center to carry out a manual image comparison without the user necessarily going to the center. The drug measuring devices can have a simpler configuration than if they had to carry out the release check themselves.

In another configuration, the activation device is a part of the drug measuring device and comprises, e.g., a software program, which can run on a control device or on a processor of the drug measuring device, as well as a local memory, in which the activation data bank with the activation data set for the user is stored. This configuration reduces the amount of data that the drug measuring device must exchange with a center during the activation phase. It is sufficient to transmit the result of the release check as well as the images of the activation image set that show the face of the user with a sufficient image quality and shall be used during a subsequent use phase to the center and, conversely, to transmit the result of the release check to the drug measuring device.

The local software program selects the images that show the face of a person completely with a sufficient image quality. The release check with the image comparison is preferably carried out in the center in order to reduce the risk of a successful manipulation. The system for the image comparison needs therefore be present only once and can be used for a plurality of drug measuring devices. It is possible, instead, to carry out the release check with the image comparison locally on the drug measuring device during the activation phase as well.

In a preferred configuration, the drug measuring device comprises an output unit, on which instructions can be outputted to a human being in a form perceptible for a human being. The drug measuring device is configured for this purpose to output on this output unit instructions on how the image or the images of the activation image set shall be generated during the activation phase. This configuration reduces the risk that the drug measuring device will not be released for the user because the user does not allow images of them to be generated in the correct manner.

One configuration of the present invention pertains, furthermore, to an activation unit, which comprises the activation device according to the present invention as well as the activation data bank with the activation data set for the user. The activation device has read access at least at times and write access to the activation data bank at least at times.

According to the present invention, the activation device releases the drug measuring device for the user when the release criterion is met. In a preferred configuration, the release comprises the step that a release message is transmitted to the drug measuring device. As soon as the drug measuring device receives the release message, the drug measuring device puts itself into a state in which it can be used for carrying out at least one drug test. The release message may comprise a password. The entry of this password releases the drug measuring device for the user. The released drug measuring device is preferably capable of transmitting a message on the result of a drug test to a receiver located at a distance in space. In addition, the activation data set is completed by a remark that the drug measuring device is released.

A use phase is preferably carried out after successful activation and release. The drug measuring device makes it possible during the use phase for a person to give a sample each repeatedly into the drug measuring device.

The testing unit checks each time after a sample has been given whether the content of at least one predefined substance is above or below the predefined limit, and it generates a result of the test. The image recording device of the drug measuring device generates at least one image of the person who uses the input unit in order to give a sample from himself or herself. The image recording device preferably generates a plurality of images with different viewing directions and/or under different light conditions during the giving of a sample.

A data processing unit checks during the use phase each time after a sample is given whether this sample has indeed been given by the user or by another person. This data processing unit is preferably arranged at a distance in space from the drug measuring device in order to make manipulations by the user difficult, and it can receive and process messages from a plurality of drug measuring devices. The data processing unit may be identical to the activation device or it may be separated from it in space. It is, however, also possible that this data processing unit is a part of the drug measuring device.

The data processing unit has read access at least at times to a use data bank, in which a use data set for the user is stored. This use data set comprises at least one image of the user, preferably two images, which show the user from different viewing directions and/or under different light conditions. This use data set is identical to the activation data set for the user in the activation data bank or it was generated with the use of the activation data set in the activation data bank. The use data set in the use data bank preferably comprises at least one image of the activation image set, which shows the user, especially preferably a plurality of images from different viewing directions and/or under different light conditions. The use data set preferably consists exclusively of at least one image, preferably of a plurality of images, of the activation image set, i.e., it comprises no reference image. This configuration ensures that only images that were generated by an image recording device of a drug measuring device and therefore show, as a rule, at least partially an input unit are used during the use phase. The risk that an image generated during the use phase is wrongly classified as not originating from the user is reduced.

As was mentioned already, the image recording device generates at least one image of the person who is giving the sample during the giving of a sample. This image or each image that was generated of the giving person during the giving of the sample is transmitted to the data processing unit used during the use phase.

The data processing unit checks during the use phase after the giving of each sample whether the transmitted image or each transmitted image shows the face of the user or else somebody or something else. For this comparison, the data processing unit compares the transmitted image or each transmitted image with the image or with at least one image that belongs to the use data set for the user in the use data bank and shows the face of the user with a sufficient image quality.

In an alternative, the data processing unit automatically decides whether the sample was given by the user for whom the drug measuring device is released or by someone else. In another alternative, the data processing unit triggers the step that a system located at a distance in space or an authorized person makes the decision on whether or not the transmitted image or each transmitted image shows the user and records the result of the decision.

In one configuration, the result that was obtained by the testing unit during the testing of the sample given is also transmitted to the data processing unit, and the data processing unit completes the use data set for the user in the use data bank by the result of the testing, preferably associated with a time stamp, which indicates when the sample was given. In a different configuration, the use data set is only completed by the result of the test if it was decided that the sample was given by the user rather than by someone else. If the sample was given by someone else, this result is stored associated with the time stamp but not necessarily with the test result.

The data processing unit preferably generates during the use phase an alarm when at least one of the following two events is detected:
  The testing unit has detected that the content of the predefined substance or of one predefined substance in the sample given is above the predefined limit.
  The data processing unit has decided that the sample was not given by the user.

The data processing unit preferably triggers the step that this alarm is outputted in a center, and in a form perceptible by a human being. An authorized person, e.g., a probation officer for the user or a custodian, may trigger a suitable step, e.g., in order to protect people in the environment of the user, and/or the user can take steps for the release to be revoked for the user.

In one configuration, it is left up to the user to select the time for giving a sample. In a preferred configuration, the drug measuring device or the data processing unit used during the use phase determines, by contrast, at least once and preferably repeatedly, a time at which a sample shall again be given, for example, according to a predefined plan. As an alternative to the determination, the drug measuring device or the data processing unit itself sets automatically the time or at least one time at which the user is to give a sample, for example, by means of a random generator.

As soon as the determined or set time or such a determined or set time has come, the drug measuring device outputs a prompt for giving a sample, said prompt being outputted in a form perceptible by a human being. The drug measuring device preferably outputs a latest permissible time for giving a sample, so that the user has time to give the sample, but the drug cannot have been decomposed in the body of the user by the time the same is to be given.

In a variant of this configuration, the use data set for the user comprises in the use data bank a predefined implementation regulation, which is assigned to the user and is available to the computer. This implementation regulation comprises specifications of how samples are to be given. The regulation preferably comprises a specification of how often and/or at what time intervals a sample is to be given. The drug measuring device or the data processing unit uses this implementation regulation in order to determine or to set itself a time at which a sample is to be given.

The drug measuring device and/or the data processing unit preferably check whether a sample was indeed given at a determined or set time. If it was detected that no sample was given, the drug measuring device or the data processing unit triggers, in turn, the step that an alarm is outputted in the center in a form perceptible for a human being.

As was mentioned already, the data processing unit checks during the use phase each time after a sample was given whether the sample was given by the user or by somebody else. The data processing unit uses for this checking the use data set for the user in the use data bank, this use data set comprising at least one image of the user, preferably a plurality of images of the user, from the activation image set, preferably with a sufficient image quality.

In one configuration, the data processing unit and the use data bank are parts of the drug measuring device. The respective result of each test, especially preferably together with a time stamp, is preferably transmitted to a central logging and data processing unit located at a distant location in space and is stored in a central logging data set for the user, e.g., in the activation data set of the activation data bank or in a special logging data set for the user. In another configuration, the data processing unit and the use data bank are separated in space from the drug measuring device. Use data sets for a plurality of users are preferably stored in the use data bank, and the data processing unit receives messages from a plurality of drug measuring devices. A message is transmitted to the testing unit each time after a sample was given. This message comprises the result, which the testing unit of the drug measuring device determined, preferably a time stamp of the time at which the sample was given and, in one configuration, at least one image of the person giving the sample and in another configuration a result obtained locally from the drug measuring device on whether the sample was given by the user or by somebody else.

The drug measuring device preferably has additionally a device code. This device code distinguishes the drug measuring device from all other drug measuring devices, which are capable of transmitting messages to the data processing unit. In one configuration, the image or each image of the activation image set comprises this device code or a device code of the image recording device of the drug measuring device. It is ensured thereby that the images of the activation image set do indeed originate from the image recording device of this drug measuring device and not from another image recording device.

The use data set for the user in the use data bank is completed by the device code of this drug measuring device at the latest after the drug measuring device has been released for the user. The data processing unit determines during the use phase with the use of the device code the use data set for the user and completes this use data set by the result of the giving of the sample.

The use data set for the user in the use data bank comprises at least one image, preferably a plurality of images, of the user, these images having been generated during the activation phase and having been recognized as originating from the user, meeting the quality criterion and preferably showing at least partially the input unit.

In one configuration, only images from the activation phase, i.e., from the activation image set, are used during the use phase in order to check whether a sample was indeed given by the user or by someone else.

In another configuration, the use data set is completed during the use phase by at least one additional image, the image recording device of the drug measuring device released for the user having generated the additional image or each additional image. The data processing unit checks whether an image, which was transmitted during the use phase to the data processing unit, meets a predefined additional criterion. This additional criterion is met only if the transmitted image has been recognized as being an image that shows the face of the user and preferably only if the image does, moreover, have a sufficient image quality.

If the additional criterion is met, the data processing unit completes the use data set for the user in the use data bank by the image. This other configuration, in which the use data set is completed during the use phase by at least one additional image, reduces the risk of a false alarm especially when the face of the user changes abruptly or gradually during the use phase, for example, because the user has a different hairstyle or is growing a beard or uses eyeglasses at times.

A configuration of the present invention pertains to a drug-measuring system, which is capable of testing a user for drugs, especially for alcohol consumption. This drug-measuring system comprises a drug measuring device, especially an alcohol measuring device,
 a use data bank, and
 a data processing unit, which is located at a distance in space from the drug measuring device.

The drug measuring device comprises again an input unit, a testing unit and an image recording device.

The use data bank comprises a use data set. Thus use data set comprises a device code of the drug measuring device as well as at least
 one image of the user, preferably at least two images of the user. These at least two images preferably show the user from different viewing directions and/or under different light conditions.

The data processing unit has read access at least at times and write access to the use data bank at least at times.

The drug measuring device is capable of generating an image of a person, who has given a sample into the drug measuring device, and of transmitting it to the data processing unit, preferably together with a device code of the drug measuring device.

The data processing unit is capable of comparing the image or each image that shows a giving person and has been transmitted to the data processing unit with at least one image, which is comprised by the use data set for the user. The data processing unit is preferably configured to compare each transmitted image with each image of the use data set.

The data processing unit is capable, furthermore, of deciding automatically whether the sample was given by the user or by another person, and of making this decision depending on the comparison between the images. As an alternative, the data processing unit is capable of triggering a decision on whether the sample was given by the user or by another person and of triggering in the process a corresponding image comparison and of detecting a corresponding decision on the result of the image comparison.

After the decision that the sample was indeed given by the user, the data processing unit is preferably capable of completing the use data set for the user by the transmitted result of the testing of the sample given. The data processing unit is preferably capable, in addition, after a decision that the sample was given by the user, of completing the use data set by the transmitted image or a transmitted image.

The drug-measuring system may be configured as a portable device, for example, as a part of a Smartphone or of a portable computer. It may also be configured for a stationary operation, for example, in the home of a user. It may also be installed in a motor vehicle of the user and it may also be in a communication connection with a vehicle immobilizer for the motor vehicle (interlock system). The vehicle immobilizer is deactivated and the person sitting in the driver's seat can drive the motor vehicle only if the person sitting in the driver's seat is recognized as the registered user and has been classified as being free from drugs. It is also possible that the drug measuring device is configured as a portable device, while the data processing unit and the use data bank are configured as stationary devices, running, for example, on the same central computer.

One configuration of the present invention pertains, furthermore, to a system and to a process for monitoring a drug measuring device, especially an alcohol measuring device. This drug measuring device is released in one configuration by the above-described process for a user and is preferably used during the use phase as was described above. The drug measuring device to be monitored comprises an input unit for giving a sample,
a testing unit and
an image recording device.
The monitoring system comprises
at least one environmental sensor,
an analysis unit,
a control device and
a first data transmission unit.

The environmental sensor or each environmental sensor of the monitoring system is capable of measuring one ambient condition each, wherein the drug measuring device is used, can be used or could be used under this ambient condition.

A desired range is predefined for each ambient condition. If the ambient condition is within this desired range, it has no harmful effect on the drug measuring device. The analysis unit is capable of receiving signals from the environmental sensor or from each environmental sensor and of detecting the result that at least one ambient condition is outside the predefined desired range. This ambient condition was measured by the environmental sensor or by an environmental sensor.

In response to the fact that the analysis unit has detected a measured ambient condition outside the respective desired range, the control device is capable of generating a signal. This signal characterizes the event that an ambient condition outside the desired range has been detected.

The control device is capable of prompting the first data transmission unit to transmit a message with this signal to at least one predefined receiver. The receiver is located outside the drug measuring device, preferably at a distance in space. The first data transmission unit is capable of transmitting this message to this receiver.

The corresponding steps are carried out in the monitoring process according to the present invention.

This monitoring system and this monitoring process are capable of detecting whether the drug measuring device is exposed to an ambient condition under which the drug measuring device cannot test a sample at all or it cannot test it with sufficient reliability, and/or whether it is exposed to an ambient condition under which the drug measuring device cannot send any messages any longer to a receiver located at a distance in space. A user may accidentally or even intentionally expose the monitored drug measuring device to such an unacceptable ambient condition in order to be able to use drugs undetected. The monitoring system and the monitoring process thus reduce the risk that the user can thus use drugs in this manner undetected. A receiver located at a remote location in space is rapidly informed of the inadmissible ambient condition.

In a preferred configuration, the environmental sensor or each environmental sensor of the monitoring system is a part of the drug measuring device to be monitored. This environmental sensor does therefore, indeed, measure an ambient condition, to which the drug measuring device is exposed. The drug measuring device comprises, furthermore, a separate power supply unit, i.e., a power supply unit, which is capable of supplying the electrical users of the drug measuring device with electricity at least at times independently from a central or stationary power supply grid. The separate power supply unit is capable, in particular, of supplying the environmental sensor or at least one environmental sensor of the drug measuring device with electricity.

In a variant of this configuration, the separate power supply unit of the drug measuring device is arranged in a housing. A housing opening sensor is capable of detecting the result that the housing is opened and/or forced open. In response to the fact that the housing opening sensor has detected an opening or forced opening of the housing, the testing unit of the monitoring system is capable of generating a signal. This signal characterizes the event that an opening or forced opening has been detected. The control device is capable of transmitting this signal to the predefined receiver or to at least one predefined receiver.

A user could attempt to put the drug measuring device out of operation by disconnecting the drug measuring device from a stationary power supply grid and by removing the separate power supply unit of the drug measuring device from the housing. The configuration with the housing opening sensor reduces the risk that the user can do this undetected. The control device causes the first data transmission unit to send the message with the signal as soon as an opening or forced opening of the housing has been detected. It is possible to equip the control device with a separate power supply unit, so that the message can be sent before the monitoring system and/or the drug measuring device cease to be supplied with electricity.

It is possible that the monitoring system is separated in space from the drug measuring device. In another configuration, at least the analysis unit, the control device and the first data transmission unit are parts of the drug measuring device. It is possible that the entire monitoring system belongs to the drug measuring device to be monitored.

In one configuration, the environmental sensor or at least one environmental sensor of the monitoring system is a part of the drug measuring device to be monitored. The drug measuring device comprises, furthermore, a second data transmission unit. The monitoring system comprises an analysis system, which is located at a distance in space from the drug measuring device. This analysis system comprises the analysis unit, the control device and the first data transmission unit. The second data transmission unit is capable of transmitting measured values repeatedly from the environmental sensor or from at least one environmental sensor, which belongs to the drug measuring device, to the analysis system.

This configuration splits the monitoring system into
environmental sensors, which belong to the drug measuring device, and
an analysis system, which is located at a distance in space from the drug measuring device. Since the environmental sensors belong to the drug measuring device, they can measure ambient conditions, to which the drug measuring device is exposed, better than if they were located at a distance in space from the drug measuring device. Since the analysis system is not a part of the drug measuring device, the drug measuring device can be configured as a lighter and/or smaller drug measuring device. In addition, a user, who wants to use drugs undetected, would have to put both the drug measuring device and the analysis system located at a distance in space out of operation before a message is sent, which is associated in some cases with a greater effort and requires more time than if the entire monitoring system were a part of the drug measuring device to be monitored. This configuration therefore leads to a further reduction of the risk that a user would put the drug measuring device out of operation undetected.

The monitoring system comprises at least one environmental sensor. The environmental sensor or at least one environmental sensor is preferably capable of measuring at least one of the following ambient conditions, to which the drug measuring device is exposed or may be exposed or could be exposed:

- a temperature in the environment of the drug measuring device,
- a change over time in a temperature in the environment of the drug measuring device,
- a humidity in the environment of the drug measuring device,
- a change over time in a humidity in the environment of the drug measuring device,
- a force or acceleration acting on the drug measuring device,
- an ambient pressure acting on the drug measuring device and a change over time in such ambient pressure, or
- the effect of a harmful substance, e.g., an acid.

The present invention will be described below on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
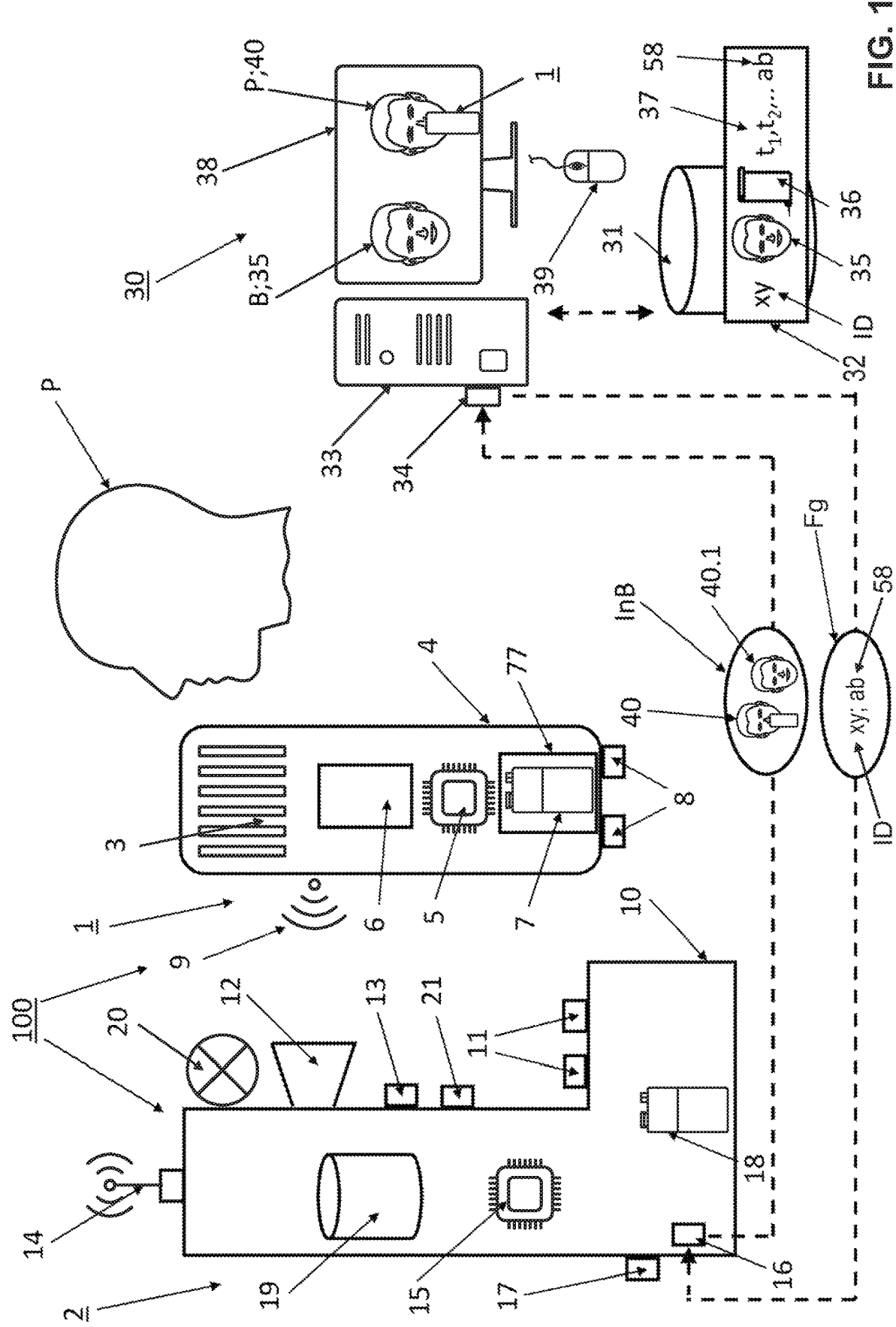
FIG. 1 is a schematic view showing the alcohol measuring device and the activation device during the activation phase.
Figure 2:
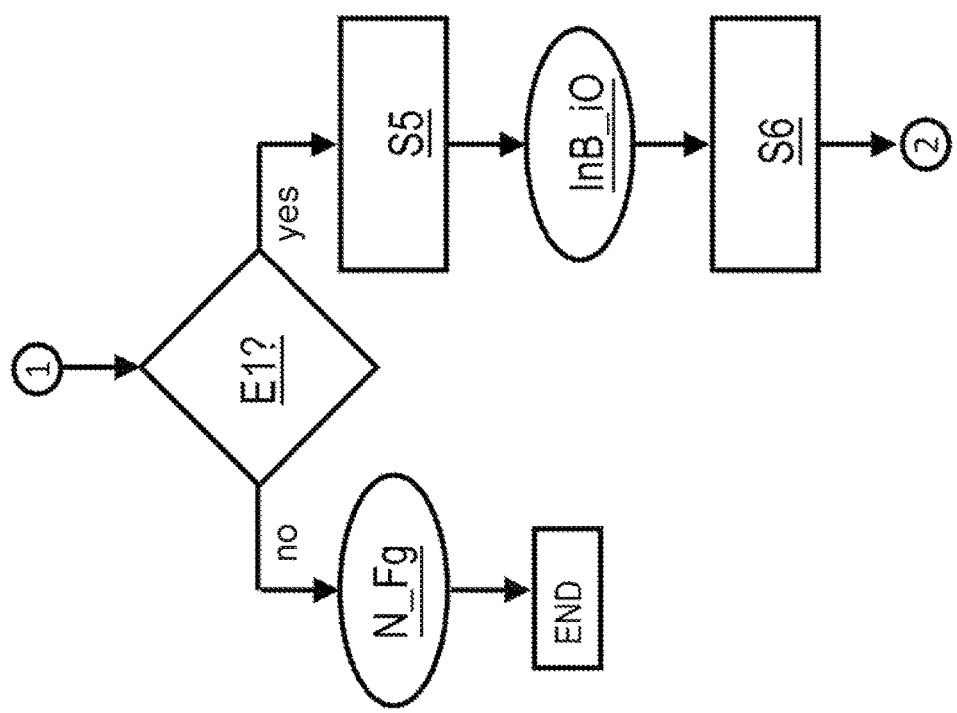
FIG. 2 is a first part of a flow chart, which shows the steps of the activation phase until the generation of the checked activation image set.
Figure 2:
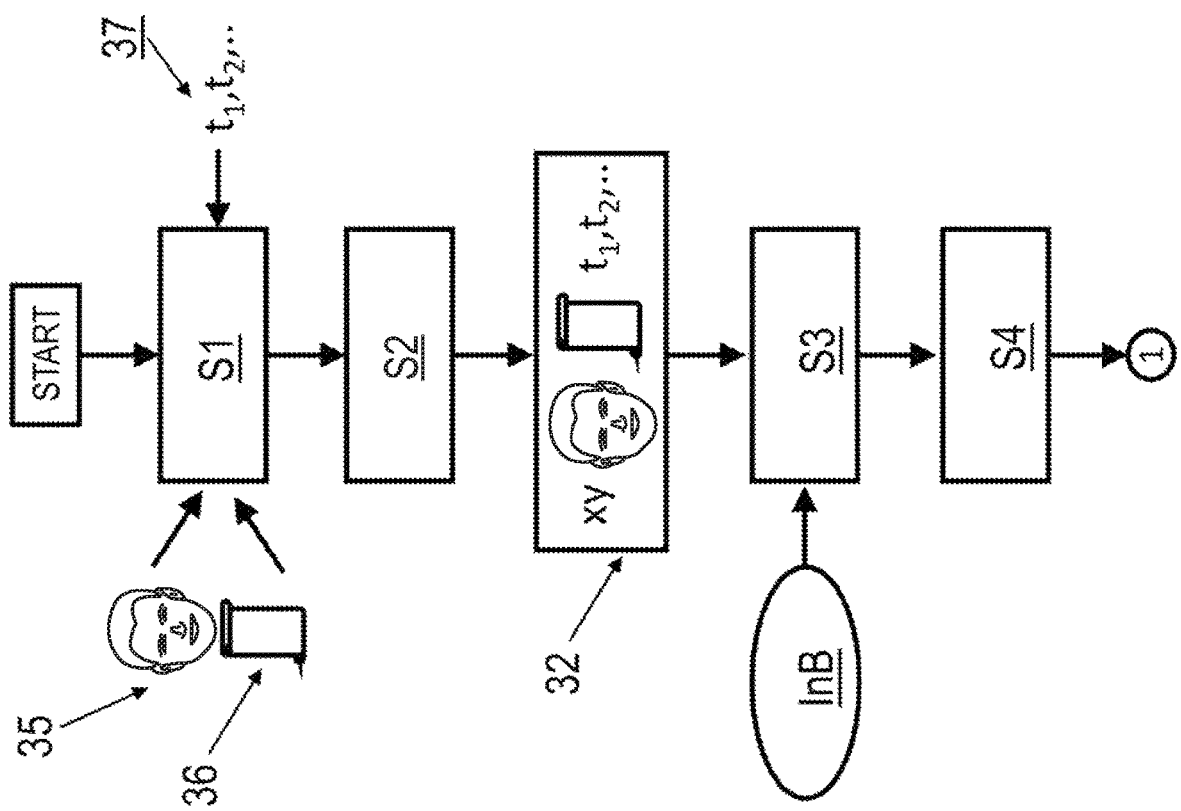
Figure 3:
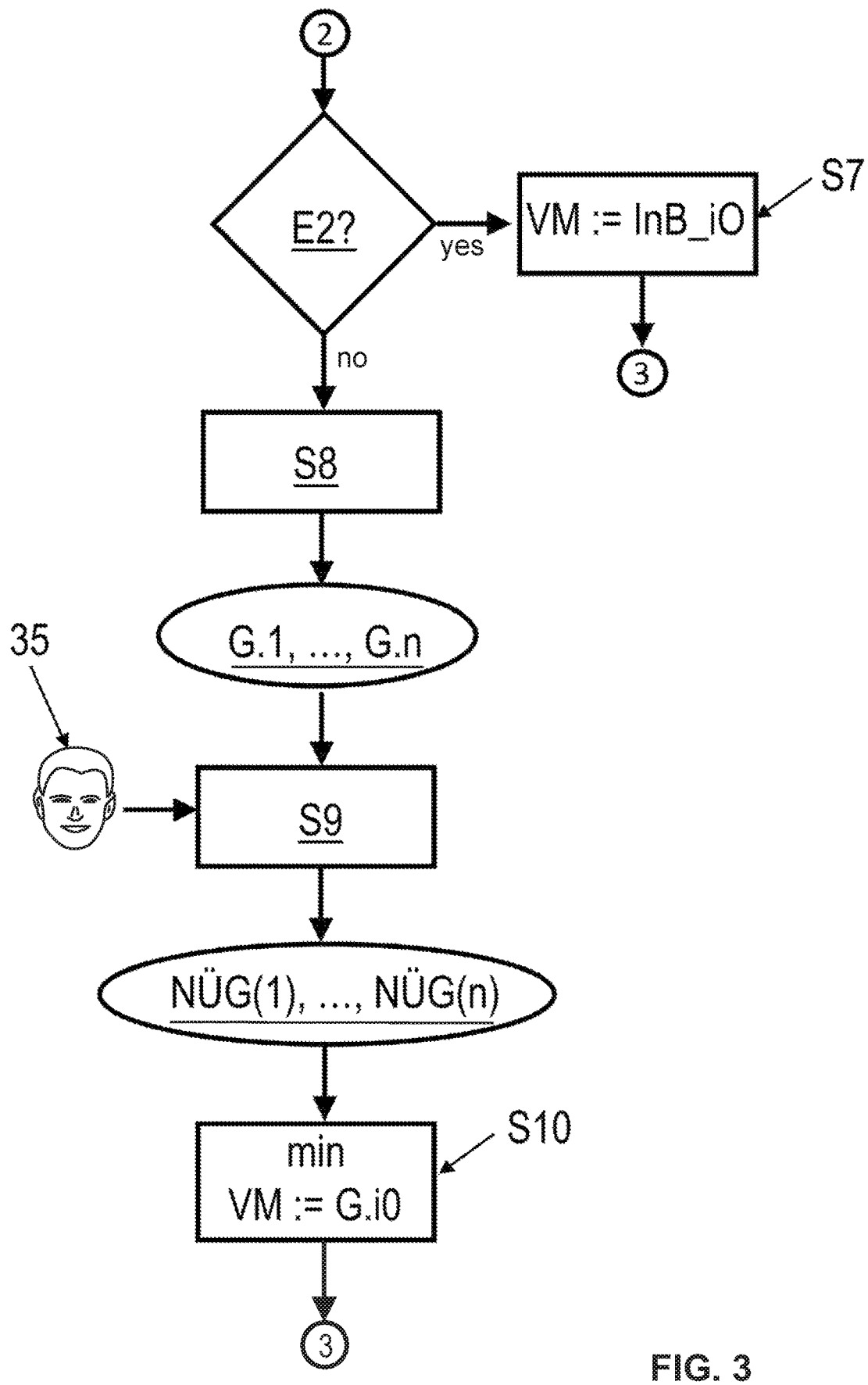
FIG. 3 is a second part of the flow chart of FIG. 2, which shows the steps of the activation phase until the generation of the comparison image set.
Figure 4:
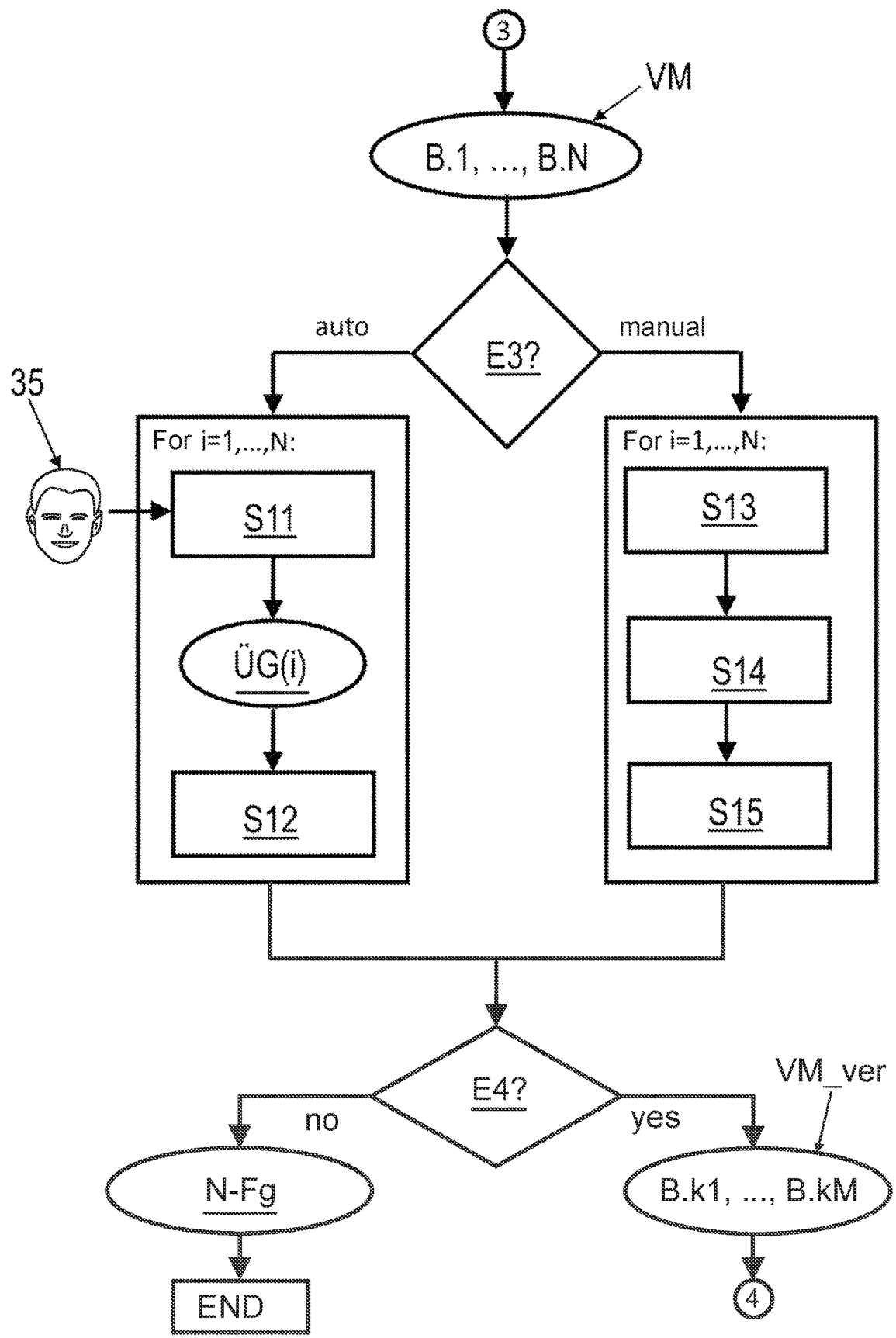
FIG. 4 is a third part of the flow chart of FIGS. 2 and 3, which shows the steps of the activation phase until the generation of the verified comparison image set.
Figure 5:
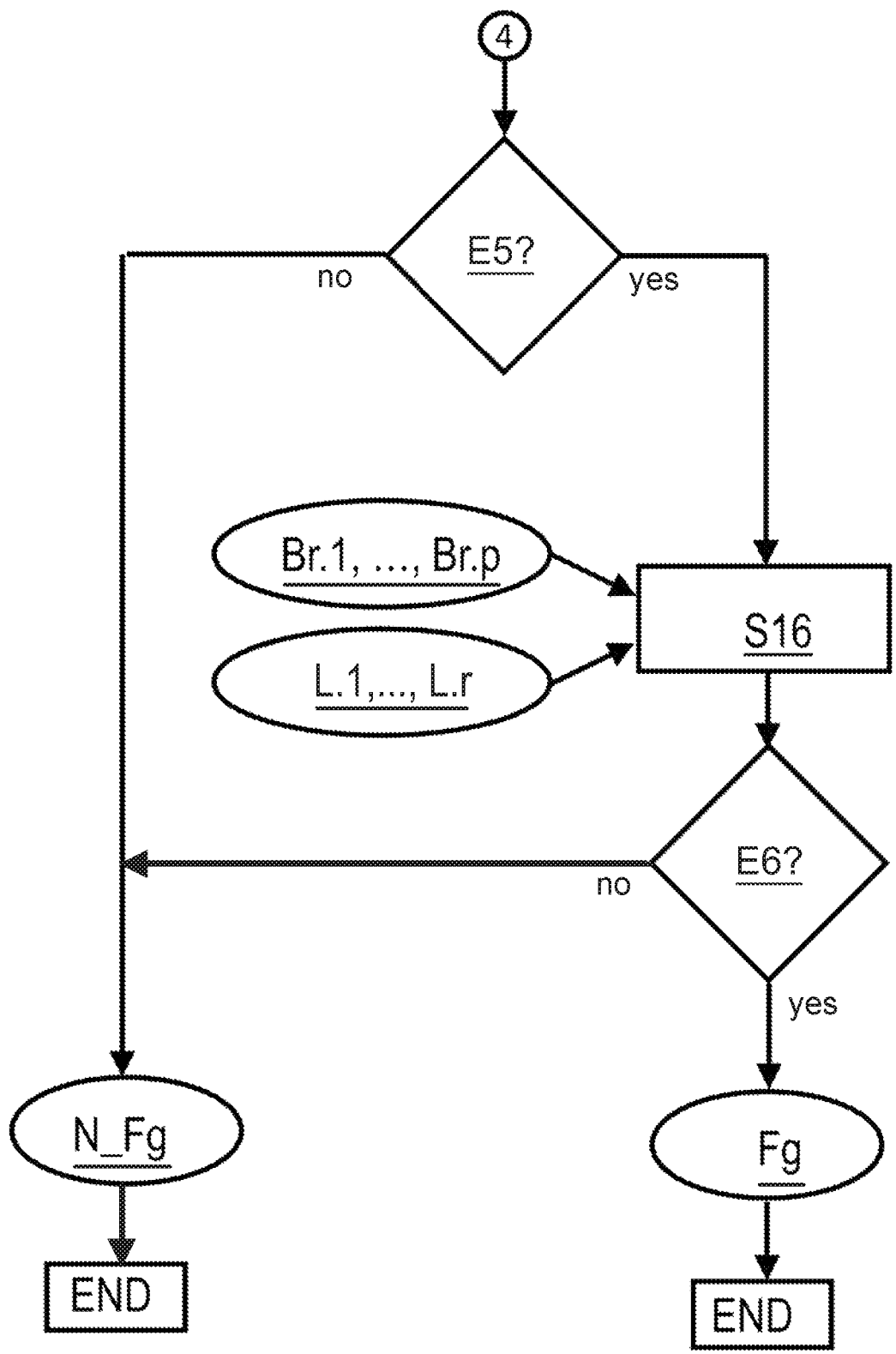
FIG. 5 is a fourth part of the flow chart of FIGS. 2, 3 and 4, which shows the steps of the activation phase until the release or other ending of the release process.

Referring to the drawings, the present invention is used in the exemplary embodiment to activate a drug measuring device in the form of an alcohol measuring device for a certain user and then to operate it. The activation comprises a release process. The user must or shall or wants to give breath samples repeatedly into the alcohol measuring device after the activation. The alcohol measuring device according to the exemplary embodiment has

- an input unit,
- a testing unit,
- optionally a light source, preferably for light in the visible range, e.g., a plurality of LEDs,
- at least one image recording device and optionally a separate image analysis unit,
- an image data memory,
- optionally an additional identification device, for example, a device for detecting fingerprints or a biometrically operating identification device, to identify a person,
- at least one internal data-processing control device, which actuates inputs and/or processes sensor values and actuates parts of the alcohol measuring device, doing so at least partly independently from the inputs and/or sensor values,
- optionally an output unit in order to output messages in a form perceptible for a human being,
- optionally a distance sensor, which measures the distance to a person or to another object in the viewing direction of the image recording device,
- optionally a brightness sensor, which measures brightness in an area in front of the image recording device,
- a system clock, which provides predefined events with time stamps,
- optionally a random generator,
- optionally a geoposition sensor for its own geoposition,
- preferably a separate power supply unit, preferably a set of rechargeable batteries, and
- a wired and/or radio-based communication unit.

In one configuration, some parts of the alcohol measuring device are arranged on a Smartphone or on another portable data processing device and the other components are arranged on a separate device, which may likewise be mobile or else stationary. The alcohol measuring device may also be configured as a single and preferably portable device or comprise a portable device and a base station. For example, the image recording device, the optional image analysis unit, the optional additional identification device, the control device or a control device, the optional distance sensor, the optional brightness sensor, the optional geoposition sensor and the power supply unit or a power supply unit may be arranged on the Smartphone and the other parts of the alcohol measuring device, especially the input unit and the testing unit, may be arranged on the separate device.

A person can give a breath sample by means of the input unit, doing so by said person holding a mouthpiece at their face and blowing in the breath sample or by said person blowing the breath sample into the input unit in a contactless manner. It is also possible that the alcohol measuring device draws in the breath sample through the input unit.

In one configuration, the testing unit comprises a plurality of sensors for pressure, humidity and/or temperature, which measure the breath sample given. The pressure sensor measures the direction of the air flow into the input unit. The testing unit has, furthermore, a preferably electrochemically operating sensor. The testing unit determines whether a sufficiently large breath sample was given, especially whether a person is indeed giving a breath sample over a sufficiently long time or else introduces air in another manner into the device and thereby mimics the giving of a breath sample that can be tested. The testing unit tests, furthermore, whether the alcohol content in a given breath sample is below or above a predefined limit. The testing unit tests, for example, whether the breath sample is free from alcohol, aside from a tolerance caused to the measuring inaccuracy. It is also possible that the testing unit measures the alcohol content in the breath sample quantitatively.

The image recording device is capable of recording a plurality of images of a person, who is giving a breath sample, one after another. The optional additional identification device is capable of detecting an additional identifying feature of a person who is giving a breath sample, e.g., a fingerprint or another biometric feature.

The light source is capable of illuminating the face of a person, who is giving a sample, so that the image recording device is capable of generating an image, which can be automatically analyzed and which shows the person with a sufficient image quality. The brightness sensor is capable of detecting whether the face is illuminated with sufficient brightness and whether it has a sufficient contrast from the background. The distance sensor is capable of measuring the distance between the alcohol measuring device and a giving person—generally: an object in front of the image recording device—and of detecting thereby whether the person is located close enough in front of the input unit. If not, it is certain that the person is not giving a breath sample from himself or herself but is blowing gas in in another manner and thereby only mimics the blowing in of a breath sample.

The optional image analysis unit is capable of checking an image from the image recording device to determine whether or not this image shows the face of a person completely and with a sufficient image quality.

The control device is capable, on the one hand, of triggering the step that data are transmitted from the alcohol measuring device to a predefined receiver, especially to the activation device described below, via the communication unit. On the other hand, the control device is capable of causing messages to be outputted on the output unit of the alcohol measuring device in a form perceptible for a human being, e.g., the prompt to give a breath sample, the message about the result provided by the testing of a breath sample or the message about whether or not an image recorded of a person who is giving the sample meets a predefined quality criterion.

The outputs of the random generator can be used automatically to generate random times at which the user shall give a breath sample, wherein these times are not foreseeable for the user.

The alcohol measuring device may comprise further parts, which detect a manipulation, e.g., in order to detect whether a person is indeed giving a breath sample or is introducing something else into the input unit and is especially indeed giving a breath sample from their body.

The communication unit is capable of exchanging data in a wired or wireless manner with an activation device located at a distance in space and with a central data processing unit located at a distance in space, which will be described farther below. The wired transmission preferably uses the Internet or a LAN. The wireless transmission may be carried out, e.g., by means of infrared waves, Bluetooth, RFID, NFC, Wireless LAN, mobile phone network, QR code or acoustically.

In one configuration, the alcohol measuring device comprises a portable testing device and a base station. The portable testing device comprises, e.g.,
- the input unit,
- the testing unit
- the optional light source,
- the image recording device or each image recording device,
- the optional additional identification device,
- the optional distance sensor,
- a first internal control device,
- a local memory,
- a power source, which is preferably rechargeable, as well as
- a housing, which holds these parts.

The base station comprises, e.g.,
- the communication unit or a communication unit,
- the optional output unit,
- the optional random generator, as well as
- preferably a second internal control device.

It is also possible that the base station comprises the image recording device or an image recording device. The base station may be detachably connected to the portable testing device and is capable of charging the power source of the portable testing device after establishing a connection. In its local image recording device, the portable testing device is capable of storing
- the time (time stamp) of the giving of a breath sample,
- optionally the geoposition at the time of the giving of the sample,
- images from the image recording device, which show a giving person, as well as
- results of the testing unit.

As soon as the portable testing device is connected to the base station in a wireless manner and/or via the contact points, the data, which have been stored in the local image data memory since the last transmission, are transmitted to the base station, and the communication interface transmits these in a wired or wireless manner to a receiver located at a distance in space. This configuration avoids the need to equip the portable testing device with the output unit and with the communication unit.

It is possible to use a Smartphone as a base station. A Smartphone already has, as a rule, an image recording device. Only a software program (an "App") needs to the installed on a commercially available Smartphone in order to make it into a base station for a testing device of the alcohol measuring device.

FIG. 1 shows such an alcohol measuring device 100 as an example, which comprises a portable testing device 1 and a base station 2 and shall be used by the user B.

The testing device 1 comprises
- a housing 4,
- an input unit 3,
- a testing unit 6,
- a separate power supply unit 7 in a housing 77,
- a wireless communication unit 9,
- contact points 8 and
- a testing device control device 5.

The base station 2 comprises
- a housing 10,
- an image recording device 12,
- a light source 20,
- a distance sensor 21, which is capable of measuring the distance to an object in front of the image recording device 12, an image data memory 19, in which images of a person can be stored, preferably together with a respective time stamp each, these images having been generated by the image recording device 12, an output unit 13, which is capable of outputting messages in a form perceptible for a human being, a wireless communication unit 14 for wireless communication, a wired communication unit 16 for wired communication, e.g., wired via the Internet, a plurality of contact points 11, a coupling point 17 for coupling the base station 2 to a stationary power supply network, a base station control device 15, and a separate base station power supply unit 18 to enable the base station 2 to be operated independently from a stationary power supply network.

If the testing device 1 is inserted correctly into the base station 2, the two devices 100 can exchange data with one another via the corresponding contact points 8, 11, and the base station 2 can charge the power supply unit 7 of the testing device 1. In addition, the devices 1, 2 can exchange data with one another in a wireless manner over a distance via the wireless communication units 9, 14. If the testing device 1 comprises an image recording device, the user can give breath samples at a distance in space from the base station 2 and a picture of them is taken in the process. The user B does not need to carry the base station 2 with him. If the testing device 1 is held close enough to the base station 2 while a sample is being given, the image recording device 12 can generate pictures of the person giving the sample with a sufficient image quality. The testing device 1 does not need to have a separate image recording device in this case.

FIG. 1 shows, furthermore, a person P, who is giving a breath sample from himself or herself into the input unit 3. Whether this person P is the user B will be checked later.

In another configuration, the alcohol measuring device 100 may be detachably connected to a mobile telephone, especially with a Smartphone. This Smartphone may be the above-mentioned Smartphone, which comprises the image recording device 12, the image analysis unit as well as additional sensors of the alcohol measuring device 100, or another Smartphone. Data that are stored in the local image data memory 19 of the preferably portable alcohol measuring device 100 are transmitted to the mobile telephone after the detection of a connection, and the mobile telephone transmits these data to the or at least one receiver located at a distance in space and outputs messages to the user.

It is also possible that the image recording device 12 is a part of the testing device 1 or of the mobile telephone. This configuration makes it possible for the user B to give a breath sample from himself or herself into the input unit 3 at any location, providing that the user carries the testing device 1 and optionally the mobile telephone with the image recording device 12 with him. The base station 2 is used to charge the power supply unit 7, and optionally to transmit images to the activation device 30 during the activation phase and to output messages to the user.

In the exemplary embodiment, the present invention is used in one configuration to configure and to release such an alcohol measuring device 100 for a (male) user B (or for a female user), who is sentenced by a court to give a breath sample from herself/herself into an alcohol measuring device according to at least one specification predefined in the sentence at regular intervals, for example, daily between 2:00 p.m. and 3:00 p.m. as well as between 9:00 p.m. and 10:00 p.m. It is also possible that the specification or a specification stipulates that the user B has to give a breath sample each at randomly selected times, i.e., at times that are not foreseeable for him. No breath sample given may contain, according to the specification, any alcohol, or have an alcohol level above a predefined limit. It is also possible that the user B undergoes a regular checking voluntarily, i.e., the user makes a commitment.

The user B must, of course, give a breath sample personally, i.e., a breath sample from their own body and not something other than a breath sample. The user B rather than someone else shall give this breath sample. The designation "user" will be used below for the person who is sentenced to give a breath sample from himself or herself repeatedly, or has voluntarily decided to do so. The person who does indeed give the breath sample is called the "giving person." Insofar as possible, it shall consequently be ensured that the giving person P is indeed the sentenced or voluntarily using user B. The user may, of course, also be a female user.

One possibility of how the user B could comply with the court-ordered condition or with the voluntary commitment is that the user visits each time a correspondingly certified sampling center or a service center and gives a breath sample there. This requires in the above example that the user B should visit a sampling center twice daily. It would not be possible to ask the user to give a breath sample immediately at a random time.

The present invention eliminates the need to do this for the user B. The user B in the exemplary embodiment will rather receive an alcohol measuring device 100 of their own, which preferably comprises a portable testing device 1. The user B can use this alcohol measuring device 100 at any location. At the least, the user B receives a portable or stationary testing device, which the user can use as home or which is installed in a motor vehicle. It is possible that the user B receives at least two alcohol measuring devices, e.g., a stationary measuring device for use at home or in the motor vehicle and a mobile measuring device for use during travel outside the motor vehicle. This configuration makes it possible to require the user to give a breath sample immediately repeatedly at a time that the user B cannot foresee.

Such a procedure for monitoring a user from a distance on how sober the user is also called "remote alcohol monitoring" (RAM). A portable device suitable for this is described, e.g., in US 2016/0161468 A1 and in US 2016/0153963 A1 as well as in US 2018/0313818 A1 (each of which is incorporated herein by reference in its entirety).

How the alcohol measuring device 100 is assigned to the user B according to the present invention and how it is activated will be described below. This activation leads to a release—or to a non-release. The term "activation" designates below the steps that are carried out to bring the alcohol measuring device 100 into the possession of the user B and to release it—or not to release it—for the user after a checking. After a successful release, the user can use the alcohol measuring device 100 during the use phase in order to give breath samples.

The term "activation" is not used, in particular, to designate processes that are carried out after the release and hence during the subsequent use phase, for example, when the alcohol measuring device 100 is switched on again after a break in operation or a repair or after maintenance.

The user B registers himself or herself in one configuration of the present invention with the activation device. The user B transmits data about himself or herself for this purpose over a secured data connection to the activation device, for example, over a secured connection on the Internet and preferably by means of encryption. The data of the user B about himself or herself comprise

- at least one reference image of at least one official document of the user B, e.g., a photo in a driver's license or in an identity card or in a passport, as well as
- if available, a computer-available likeness or a copy of a document that shows the sentence.

The document on the sentence preferably specifies especially a condition as to the frequency and optionally the times at which the user shall give a breath sample, or that random times shall be selected, as well as the desired result of each measurement of the breath sample, e.g., that no breath sample shall contain alcohol.

In addition, the transmitted data preferably comprise

- an individual identification code of the user B,
- optionally an additional identifying feature of the user B, e.g., a digitally scanned fingerprint or another biometric feature,
- a mailing address to which an alcohol measuring device 100 for this user shall be sent,
- a desired manner of data transmission from an alcohol measuring device 100 of the user B to the activation device during an activation phase,
- a desired manner of data transmission to a central data processing unit during a subsequent use phase of the alcohol measuring device 100,
- the manner in which the output unit 13 shall output messages to the user B, for example, optically, acoustically and/or by touch,
- the language in which the output unit 13 shall output messages to the user,
- properties of the alcohol measuring device 100 desired by the user B, e.g., stationary or mobile, and/or
- data on payment for the alcohol measuring device 100.

The two desired types of data transmission may be identical or different. For example, a data transmission with a higher data security and possibly lower transmission rate will be used during the activation phase than during the use phase.

In one configuration, an authorized person checks the transmitted data, especially the copy of the official document. If the transmitted data are correct, the authorized person releases the registration. It is also possible that the activation device releases the transmitted data automatically and thereby registers the user B. The user B needs to disclose himself or herself to no one or only to an authorized person at the time of the registration. The authorized person may be positioned at a distance in space from the user B.

In a different configuration, the user B visits an issue center or a service center and is registered there. The user B can present there an official document with a photo of himself or herself—or even only a photo. Or at least one image of the user B is generated in the issue center or service center.

A registration data set is preferably generated as a consequence of the registration. This data set detects the images of the user B, which are generated during the registration, as well as optionally a copy of the sentence. These images are called the "reference images" of the user B.

After the user B has registered successfully, an activation phase is carried out, which will be described below.

An activation data set is created for the user B in a data bank of the activation device, and the registration data set is used for this. This activation data set comprises the transmitted data of the user, i.e., especially the copy of the official document and hence at least one reference image, e.g., from the official document, and the copy of the sentence or voluntary commitment. The activation data set for the user B is secured against unauthorized read access and against manipulation from the outside in a suitable manner.

FIG. 1 shows the alcohol measuring device 100 and, furthermore, the activation device 30, which is responsible for a plurality of alcohol measuring devices in the example shown and is located at a distance in space from the alcohol measuring devices. It comprises the following parts in the exemplary embodiment:

- a data-processing central computer 33, which carries out the release check,
- an output unit 38, which is capable of displaying a comparison with at least two images,
- an input unit 39, with which an authorized person can "communicate" the result of an image comparison by a user input of the activation device 30, as well as
- a wired communication unit 34.

The activation device 30 has read access at least at times and write access at least at times to an activation data bank 31 with an activation data set 32 for the user B.

Data can be transmitted from the base station 2 in a wireless manner, e.g., over the Internet, via the wired communication unit 16 and the wired communication unit 34 to the central computer 33. A wireless transmission is possible as well.

The activation data set 32 for the user B comprises after successful registration and before the release process

- an unambiguous identification code ID of the user B, for example, a code of an official photo ID,
- at least one reference image 35, which shows the user B,
- optionally an additional identifying feature of the user B,
- optionally a computer-available copy 36 of the sentence or voluntary commitment,
- a computer-evaluable implementation regulation 37, which specifies how the user B has to comply with the conditions of the sentence or commitment, and
- optionally additional data on himself or herself, which the user B has transmitted.

An alcohol measuring device 100 is selected now for this registered user B from a stockroom holding a plurality of not yet configured and personalized alcohol measuring devices. The alcohol measuring device 100 is selected such that the user B can meet the condition or each condition according to the transmitted sentence or commitment with this device and the device optionally possesses the transmitted properties desired by the user B. The alcohol measuring device 100 is preferably certified correspondingly. The selected alcohol measuring device 100 is configured for the user B corresponding to the specifications in the activation data set 32, and, e.g., the type of the data transmission and/or of the output of messages is configured. It is not yet released for the user B even after this configuration.

The selected alcohol measuring device 100 comprises a device code 58, which distinguishes this alcohol measuring device 100 at least from all other alcohol measuring devices which are used in an area of responsibility of the activation device and/or of the central data processing unit. The activation data set 32 for the user B is completed by this device code 58. A defined alcohol measuring device 100 is thus assigned to the user B and it is suitable for checking the user B. However, the alcohol measuring device 100 not yet released for the user.

It is possible that a plurality of alcohol measuring devices are assigned to the user B, e.g., a stationary device and a mobile device or two devices of the same type in order to create redundancy. The activation data set is correspondingly completed for the user B by a plurality of device codes.

If the user B has transmitted a mailing address, the step that the alcohol measuring device 100 or each alcohol measuring device 100 assigned to the user B will be sent to that mailing address from a central warehouse is triggered in one configuration. As soon as the user B has received the alcohol measuring device 100 or an alcohol measuring device 100 and has confirmed the reception, a message is generated and transmitted to the activation device that the registered user B has now received the alcohol measuring device 100 assigned to him.

It is also possible that a message is transmitted to the registered user B that the user B can pick up the alcohol measuring device 100 assigned to them at an issue center specified in the message. A corresponding message is transmitted in this configuration to the activation device 30 as soon as the user B has picked up the alcohol measuring device 100 at the issue center.

In another configuration, a user B, who is not yet registered, generally: a person, goes to a registration office and registers himself or herself there, for example, by the person submitting an official document. The above-described steps for registering a user are triggered from this registration office or are carried out in the registration office itself. In particular, a decision is made in this connection on whether the person who has visited the registration office is the user B to whom the sentence or commitment pertains. An authorized person preferably checks the submitted official document. It is possible, albeit not necessary, that the person submits the document showing the sentence or commitment in addition to the official document.

A suitable alcohol measuring device 100 is made available to the user B after successful registration. The registration office keeps at least one suitable alcohol measuring device in stock in one configuration, and the user B takes a suitable device with them from the registration office. In an alternative configuration, the alcohol measuring device 100 is selected from the central warehouse and is sent to the user B, e.g., to their mailing address. This configuration avoids the need to have to stock suitable alcohol measuring devices at each registration office.

After the alcohol measuring device 100 has been made available to the user B in one of the above-described manners, the activation data set 32 for the user B is completed by the device code 58 of the alcohol measuring device 100, cf. FIG. 1.

The configured alcohol measuring device 100 is assigned now to the registered user B in all these configurations of the registration, and it is in the possession of the user B, but it is not yet released for the user B. It will be described below how the alcohol measuring device 100 is released—or also not released—for this user B after a checking.

A person P gives a breath sample into the input unit 3 of the assigned alcohol measuring device 100 several times one after another. The image recording device 12 generates at least one image of the person P, who is giving the breath sample, each time the user is giving a sample. In one configuration, each correctly taken image shows the face of a giving person P completely as well as the testing device 1 or at least the input unit 3. It is specified in another configuration that some generated images shall show the giving person with the testing device 1 and other generated images shall show the giving person P without the testing device 1. The position and/or the orientation of the head of the giving person P relative to the image recording device 12 shall vary in one configuration from one sampling to the next, so that images that show, as a whole, the giving person from different viewing directions, are generated at the times at which these samples are given.

Furthermore, the base station control device 15 preferably actuates the light source 20 such that the face of the giving person P is illuminated differently, so that, on the whole, images with different illuminations, which show the face of the giving person P, are generated. This increases the security at the time of a subsequent image comparison.

The base station control device 15 preferably causes the generated images to be stored in the image data memory 19.

If the samples are given correctly, each generated image shows the face of the user B completely and, on the whole, a sufficient number of images are generated, which show the face of the user B with a sufficient quality and from different viewing directions and with different illuminations. However, the following errors may occur:

Insufficiently generated images show the face of the user B completely and with a sufficient quality.

The face of the user B shown in the image does not appear with sufficient brightness or with sufficient clarity.

The images do not show the face of the user B from sufficiently different viewing directions and/or with sufficiently different light conditions.

At least some images do not show the face of the user B but the face of another person or they do not show the face of a person completely but they show the face only incompletely; they show another body part or they do not show a person but they show another living being or something else.

In one configuration, the alcohol measuring device 100 instructs the giving person during the giving of breath samples. For example, the alcohol measuring device 100 always generates a message in a form perceptible for a human being as to the position and/or orientation the face of the giving person P shall have relative to the image recording device 12 of the alcohol measuring device 100 during this giving, wherein this position and/or orientation varies from one giving to the next. The alcohol measuring device 100 preferably gives instructions in a form perceptible for a human being, e.g., instructions that specify the required viewing direction or change in the viewing direction of a giving person and/or which prompt the person P to use the alcohol measuring device 100 in front of different backgrounds. The optional light source of the alcohol measuring device 100 preferably varies the illumination of the face of the giving person P automatically in order to generate images under different light conditions. The optional image analysis unit of the alcohol measuring device 100 checks whether a recorded image does indeed show the face of a giving person P completely and with an image quality sufficient for a subsequent comparison, especially whether the face of the giving person P is sufficiently illuminated. If the image does not meet this requirement, it is discarded.

In a preferred configuration of the exemplary embodiment, it is, however, the central activation device 30 rather than the alcohol measuring device 100 that checks which images do indeed show the face of the user B and which images show another person or something else. Whether images were generated, as a whole, from sufficiently different viewing directions and/or under sufficiently different light conditions is preferably also checked centrally rather than locally.

The alcohol measuring device 100 preferably generates a message as soon as the person P has given a sufficient number of samples and a sufficient number of suitable images of the giving person P have been generated with a sufficient quality and under different viewing directions and/or light conditions and this is optionally confirmed by the giving person P.

In one configuration, the base station control device 15 prompts after a corresponding user input that all the images recorded so far be displayed on the output unit 13 of the base station 2. A person P, who uses the alcohol measuring device 100, can again delete individual displayed images. In addition, the alcohol measuring device 100 preferably detects a user input on whether additional images shall still be generated or whether all the images to be transmitted have now been taken and displayed.

A message is preferably transmitted by means of the communication units 16 and 24 to the activation device 30. In one configuration, the user B triggers this message. In another configuration, the alcohol measuring device 100 automatically triggers the transmission of the message as soon as a sufficient number of images of the giving person P have been generated with a sufficient quality.

The message comprises in both configurations an activation image set InB with the images that were generated during the samplings and show the face of the user B completely in case of a correct procedure, they ideally show the face from a sufficient number of different viewing directions and under sufficiently different light conditions. FIG. 1 shows as an example two images 40 (face of user B with alcohol measuring device 100) and 40.1 (face without alcohol measuring device 100). Both images 40, 40.1 as well as additional images were generated by the image recording device 12 and were transmitted as part of the activation image set InB to the activation device 30. The message optionally comprises additionally an additional identifying feature of the giving person P, e.g., a fingerprint or another biometric feature.

In case of an incorrect procedure, the activation image set InB may show too few images that show the face of the user B with a sufficient quality or show an image of the user B with sufficient quality but not from each required viewing direction and/or not in each required illumination. It is, of course, possible that at least some images do not show the user B but another person.

The message preferably comprises additionally the device code 58 of the alcohol measuring device 100 used and/or an identification code ID, which was given by the user B in advance at the time of the registration and was assigned automatically.

It is also possible that the user B brings a data storage medium with the device code 58 and with the images 40, 40.1 of the activation image set InB to a registration office, which triggers the step of generating the message with the device code 58 and with the images 40, 40.1 and of transmitting it to the activation device 30.

The activation device 30 searches in the activation data bank 31 for the activation data set 32 for the registered user B to whom an alcohol measuring device 100 with this device code 58 and/or with this identification code ID is assigned. If no activation data set is found, an error message is outputted. The following steps are carried out otherwise:

The central computer 33 preferably checks first which transmitted images show the face of a person P completely with a sufficient image quality, preferably together with an input unit 3. The transmitted images that do not meet these requirements are preferably sorted out by calculation and will not be used for the next steps.

The images 40, 40.1 of the activation image set InB, which were not sorted out and which were transmitted as part of the message to the activation device 30, are compared with the reference image 35 or with each reference image 35 of the registered user B, and the activation data set 32 found comprises the reference image 35 or each reference image 35.

In a preferred configuration, the central computer 33 prompts an authorized person to perform a comparison. The reference image 35 or each reference image, which is contained in the activation data set 32 of the registered user B, is displayed on a screen of the output unit 38. The images 40, 40.1 or a respective image that was transmitted as a part of the activation image set InB with the message and was not sorted out is displayed on the same screen 38 or on another screen. FIG. 1 shows as an example that a reference image 35 and an image 40 of the activation image set InB are displayed on the screen 38.

The authorized person compares the images 35, 40, 40.1 and decides whether all these images show the user B or not. In one configuration, this authorized person has no read access to the copy 36 of the official documents or to the copy of the sentence, which is contained in the activation data set 32 for the user B. Requirements on data protection are thus complied with. The user B does not need to disclose himself or herself as a sentenced person or alcoholic to this authorized person.

In one configuration, the central computer 33 compares first automatically the transmitted images that were not sorted out with the reference image 35 or with each reference image 35 in the activation data set 32. The step of displaying the images for comparison to the authorized person is only triggered in one configuration if the activation device 30 determines a sufficiently high degree of agreement between at least one image 40 of the activation image set InB, which was not sorted out, and a reference image 35 of the activation data set 32. It is avoided thereby that the authorized person should deal with image comparisons for images that obviously do not show the user B.

In another configuration, the images of the activation image set InB that were not sorted out or even all images of the activation image set InB are displayed to the authorized person for comparison.

By means of the input unit 39, the authorized person gives their decision about which displayed images of the activation image set InB agree with the displayed reference image 35 or with a displayed reference image 35. The activation device 30 detects the entry of the authorized person.

In a third configuration, the central computer 33 carries out the image comparison in pairs automatically without an authorized person being involved. The central computer 33 calculates a degree of agreement between the reference image 35 or a reference image 35 and an image 40 of the activation image set InB during the pair-by-pair image comparison and decides whether this degree of agreement is above a predefined lower limit or not.

The images that do indeed show the complete face of the user B with a sufficient quality according to the manual input or according to the automatic pair-by-pair comparison are selected from the transmitted images by the automatic and/or manual comparison.

The central computer 33 checks whether the selected images together meet a predefined release criterion, especially whether the selected images show the user B from a sufficient number of different viewing directions and/or under sufficiently many different light conditions.

If the selected images meet the release criterion, the alcohol measuring device 100, which is assigned to the registered user B and is already in the possession of the user B, is released for this user B. The activation data set 32 for this user B is completed in the activation data bank 31 by a corresponding piece of information as well by at least one selected image 40, preferably by each selected image 40, 40.1, of the activation image set InB. Consequently, the activation data set 32 preferably comprises after the release a plurality of images, which show the face of the user B with a sufficient image quality from different viewing directions and/or under different light conditions.

A release message Fg about the release is transmitted to the alcohol measuring device 100 or to a computer of the user B. The alcohol measuring device 100 preferably outputs this release on its output unit 13.

In one configuration, the activation device 30 additionally transmits a sampling schedule or an implementation regulation 37 to the now released alcohol measuring device 100 in a form that the control device 5 or 15 of the alcohol measuring device 100 can automatically analyze. This is defined as a condition on how often and/or at what times the registered user B shall give a breath sample, or that the alcohol measuring device 100 shall automatically set the times at which samples shall be given, e.g., according to a random principle. For example, the optional random generator shall be used for this during the use phase. The condition preferably also comprises the desired result that this breath sample shall have.

If, by contrast, the activation device 30 has determined that the release criterion is not met, a corresponding message is transmitted to the alcohol measuring device 100. The alcohol measuring device 100 is not released for the user B at least for the time being.

FIG. 1 schematically shows such a release message Fg. This comprises the identification code ID of the user B as well as the device code 58 of the released alcohol measuring device 100.

As it was just described, the central computer 33 sorts out by calculation the transmitted images that do not show completely the face of a person P with a sufficient image quality. In one configuration, the central computer 33 then automatically groups the images that were not sorted out. All images of one group show the same person. Two images in two different groups always show two different persons. It is possible that a group with images is formed that do not show completely the face of a person with a sufficient image quality. If all images are assigned to the same group during this grouping, they show the face of the same person P. The central computer 33 automatically compares the images of this group with the reference image 35 or with each reference image 35 or it triggers the process that this comparison is carried out by an authorized person as was described above.

If the central computer 33 has formed, by contrast, at least two different groups, the central computer 33 automatically selects a group, namely the group whose images show the face of the user B—in general, the group that has the lowest degree of non-agreement with the reference images of the face of the user B. The central computer 33 compares for this selection the images of one group with the stored reference image 35 or with each stored reference image 35.

As an example, FIG. 2 through FIG. 5 show by means of a flow chart the steps that are carried out during the activation phase. The following steps are carried out here:

In step S1 the activation device 30 receives data on the registered user B, especially a reference image 35, a copy 36 of the sentence or commitment and an implementation regulation 37.

In step S2, the central computer 33 creates the activation data set 32 for the user B in the activation data bank 31 on the basis of these data.

In step S3, the activation device 30 receives a message with the activation image set InB.

In step S4, the central computer 33 checks whether this message with the activation image set InB has arrived in time, i.e., within a predefined time period, at the activation device 30 and whether this message is authorized.

If the message has not arrived in time or if it is not authorized (branch "no" of the decision E1?), the activation device 30 generates a message N_Fg that the alcohol measuring device 100 is not released for the user B. The activation phase is thus ended without a release.

If branch "yes" is passed, the central computer 33 sorts out in step S5 from the activation image set InB the images that do not show the face of a person completely and/or with a sufficient image quality.

Step S5 yields a checked activation image set InB_iO, which comprises the images that were not sorted out. Each image of the checked activation image set InB_iO shows the face of a respective person P completely and with a sufficient quality. It is to be checked which images of the checked activation image set InB_iO show the user B and which images do not.

The central computer 33 checks in step S6 whether all images show the face of the same person or faces of different persons.

In decision E2?, the central computer 33 decides whether all images of the checked activation image set InB_iO show the face of the same person P (branch "yes") or faces of at least two different persons (branch "no").

The central computer 33 creates a comparison image set VM. In step "yes" this is the entire checked activation image set InB_iO (step S7).

In step S8 of the branch "no" the central computer 33 groups the images of the checked activation image set InB_iO into n groups G.1, . . . , G.n, n>=2. Each image of a group G.i (I=1, . . . , n) shows the same person. Two images of two different groups G.i, G.j (i≠j) show two different persons.

In step S9, the central computer 33 calculates for each group G.i a degree NÜG(i) of the non-agreement between the group G.i and the reference image 35 or the reference images. In case of a plurality of reference images, the central computer 33 uses the lowest degree of non-agreement as the degree of non-agreement of the group G.i.

In step S10, the central computer 33 determines the group GA that has the lowest degree of non-agreement NÜG (i0) with the reference images 35 ("min"). This group GA is used as the comparison image set VM when passing through the branch "no".

The N images of the comparison image set VM shall be B.1, . . . , B.N in both cases. It is decided in the decision E3? based on a condition whether the image comparison shall be performed automatically (branch "auto") or manually (branch "manual").

In step S11 of the branch "auto" the central computer 33 calculates for each image B.i (i=1, . . . , n) a respective degree of agreement ÜG(i) between the image B.i and the reference images 35 or the reference image 35. If the activation data set 32 comprises a plurality of reference images of the user B, the maximum degree of agreement between the image B.i and a reference image 35 is used.

In step S12, the central computer 33 checks whether the degree of agreement ÜG(i) of the image B.i is above a predefined agreement limit and the result is thus determined that the image B.i does show the face of the user B with sufficient certainty and not the face of another person.

In step S13 of the branch "manual" the central computer 33 prompts the display of the image B.i as well as of the reference image 35 or of at least one reference image 35 on the screen 38.

In step S14, the central computer 33 detects an input of an authorized person, who made this input, e.g., with the input unit 39.

In step S15, the central computer 33 decides on the basis of the input by the authorized person whether the image B.i shows the face of the user B with sufficient certainty or another face.

Both branches yield a set of images. The central computer 33 decides in the decision E.4? whether at least one image shows the face of the user B with sufficient certainty. The central computer 33 preferably checks additionally whether at least one image shows the face of the user B with sufficient certainty and whether it additionally shows the testing device 1 or the input unit 3.

If the decision E.4? is negative (branch "no"), the activation device 30 generates a message N_Fg that the alcohol measuring device 100 is not released for the user B. The activation phase is thus ended without a release.

In case of a positive decision (branch "yes"), there is a verified comparison image set VM_ver with kM images B.k1, . . . , B.kM, where the kM images B.k1, . . . , B.kM show the face of the user B with sufficient image quality with sufficient certainty.

In the decision E.5? the central computer 33 decides whether this verified comparison image set VM_ver comprises a sufficient number of images, i.e., whether the user B has generated and transmitted a sufficient number of images, which show their face and optionally additionally the testing device 1 or the input unit 3 with a sufficient image quality and with sufficient certainty. The central computer 33 checks now, for example, whether the number kM is greater than or equal to a predefined minimum number or not.

If this is not the case (branch "no"), the activation device 30 generates a corresponding message N_Fg, and the activation phase is ended without release.

If the verified comparison image set VM_ver comprises a sufficient number of images, the central computer checks in step S16 whether these images do as a whole show the user B in the predefined viewing directions. A set Br.1, . . . , Br.p of predefined viewing directions and a set L.1, . . . , L.r of different light conditions (illuminations) are predefined for this in a computer-available form. For each predefined viewing direction Br.i and for each predefined light condition L.j, there must be in the verified comparison image set VM_ver at least one image which shows the face of the user B, who is looking in the viewing direction Br.i relative to the image recording device 12 of the base station 2, under the light condition L.j.

If this is not the case (branch "yes" of the decision E.6?), the activation device 30 releases the alcohol measuring device 100, which is already in the possession of the user B, for the user B and generates a corresponding release message Fg. The activation data set 32 for the user B is completed by corresponding information.

The activation phase is otherwise ended again without a release (branch "no" of the decision E.6?).

In an alternative configuration, a user B, who is not yet registered—or an already registered user B—visits a registration office, at which there is at least one alcohol measuring device 100, which is suitable for the user B. As was already described above, user B registers himself or herself at this registration office. A reference image 35 from an official document as well as a likeness or a copy 36 of the sentence are transmitted from this registration office to the activation device 30.

In one embodiment of this alternative configuration, an alcohol measuring device with an image recording device, which is located in the registration office, is used for the purpose of a release for the user B, even if the user B is already in possession of an alcohol measuring device 100. The user B brings with him, for example, the not yet released alcohol measuring device 100 to the registration office. Or else an alcohol measuring device other than the alcohol measuring device 100 in possession of the user B is used for the release process. The image recording device 12 of this alcohol measuring device 100 generates, as was described above, a plurality of images of the person who has visited the registration office, and generates in this manner the activation image set InB. The risk that the activation image set InB does not comprise sufficiently suitable images is reduced. The images of this activation image set InB are compared to the reference image 35 or with each reference image 35, which belongs to the activation data set 32 for the registered user B. This comparison can thus be carried out, as was described above, by an authorized person in a center, automatically by the activation device 30 or by an authorized person in the registration office. If the release criterion is met, the alcohol measuring device 100 already assigned to the registered user B is released for the user B. It is sufficient that the registration office keeps a suitable alcohol measuring device available. It is possible, but not necessary, for the user B to bring with them an alcohol measuring device 100 assigned to them from the registration office. It is also possible that the user B brings with them the alcohol measuring device 100 assigned and handed over to them for the purpose of release to the registration office and later takes it with him.

The configuration just described, namely, that a registered user B visits a registration office, is carried out in one configuration if the activation device 30 has decided after a manual and/or automatic image comparison that the transmitted activation image set InB does not meet the predefined release criterion. This checking result may be incorrect, for example, because the reference image 35 or each reference image 35 from the official document has a poor image quality. The user B can present the official document in the physical form at the issue center. An authorized person in the registration office compares the official document with the person and with images of the activation image set InB, which the image recording device 12 of the alcohol measuring device 100 generated during the activation phase. In addition, additional images of the user B can be generated in the registration office.

A date by which the user B must have concluded the registration and the release of an alcohol measuring device 100 is preferably predefined, e.g., in the sentence. If the user B does not meet this goal, the activation device 30 ends the activation phase without release and preferably generates a corresponding message N_Fg.

After the alcohol measuring device 100 with the device code 58 has been released for the registered user B, a subsequent use phase is carried out. The duration of this use phase may be predefined in the sentence and may end, e.g., after the end of a probation period or may be limited by the duration of the certification of the alcohol measuring device 100. The use phase may also be unlimited.

Figure 6:
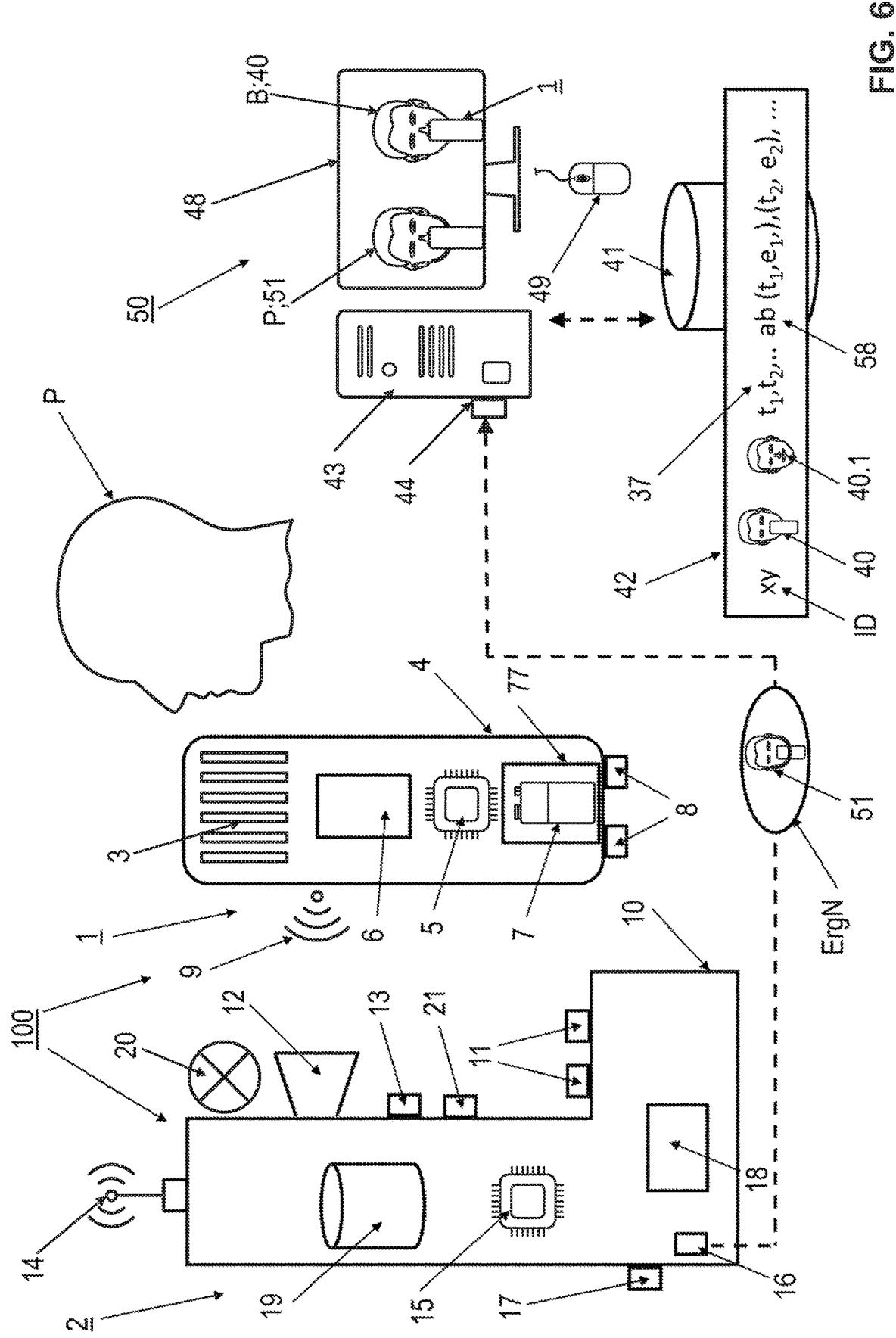
FIG. 6 is a schematic view showing the alcohol measuring device and the central data processing unit during the use phase.

FIG. 6 shows how the alcohol measuring device 100 is used during the use phase. Identical reference numbers have the same meanings as in FIG. 1. In the configuration shown, the testing device 1 tests locally the breath sample given for its alcohol content.

A central data processing unit 50 is used during the use phase. This central data processing unit 50 may be identical to the activation device 30 or it may be separated from it in space. The central data processing unit 50 comprises
  a central computer 43,
  a wired communication unit 44,
  an output unit 48 and
  an input unit 49.

The central data processing unit 50 decides on the basis of an image comparison whether a breath sample given into the alcohol measuring device 100 was indeed given by the user B or by someone else.

The central data processing unit 50 has read access at least at times and write access at least at times to a use data bank 41 with a use data set 42 used during the use phase for the user B. This use data set 42 comprises
  at least one image, preferably a plurality of images 40, 40.1, which was/were transmitted as part of the activation image set InB to the activation device 30,
  optionally the identification code ID of the user B,
  the device code 58 and
  optionally an additional identifying feature of the user B, e.g., a fingerprint.

The central data processing unit 50 has read access at least at times to the activation data bank 31 and thus to the activation data set 32 for the registered user B—or to a copy 42 of this activation data set 32, which copy is used during the use phase in order to add entries. The "use data set 42" for the user B, which is used during the use phase, will be referred to below. The central data processing unit 50 automatically decides during the use phase whether the registered user B complies with the conditions of the sentence registered in the use data set 42 or not and/or it triggers the step that an authorized person will take this decision. This decision is preferably repeated regularly, e.g., at least once daily.

The central data processing unit 50 and the activation device 30 may be embodied physically by means of the same data processing unit or with different data processing units, also at different locations.

During the use phase a person P gives repeatedly a breath sample into the input unit 3 of the released alcohol measuring device 100. The image recording device 12 generates at least one image 51, which shows the face of the person P giving the sample. The optional distance sensor 21 of the alcohol measuring device 100 determines whether a person P is indeed sitting in front of the image recording device 12 and is positioned close enough to the input unit 3. This reduces the risk that even though a person P is sitting or standing in front of the image recording device 12 and at least one image 51 is taken of this person P, this person P is not giving a breath sample but the user is giving something other than a breath sample, or even though an image of the face of the user B is generated, a breath sample is being given by a person other than the user B. The brightness sensor detects the undesired event that the image recording device 12 or an optional light source 20 of the alcohol measuring device 100 or another light source have been covered, which could be done with the aim of having a person other than the registered user B give a breath sample without this being detected, or that these units failed to operate.

In one configuration, a computer-available sampling schedule or an implementation regulation 37 was transmitted to the alcohol measuring device 100. The control device 5, 15 of the alcohol measuring device 100 registers the time at which the last breath sample was given; it has read access to the its own system clock and outputs a message when the registered user B shall again give a breath sample according to this implementation regulation 37. These messages support the user B to indeed comply with the conditions or with each condition of the sentence. In one configuration, the implementation regulation 37 further specifies how long a person shall blow a breath into the input unit 3, i.e., how long this person P shall exhale into the input unit 3 of the alcohol measuring device 100. The testing unit 6 checks whether the person P giving the breath sample is indeed blowing breathing air in for as long as required. In one configuration, the output unit 13 outputs a message that breathing air was not blown in long enough and/or that breathing air is now being blown in long enough.

In one configuration, the control device 5, 15 of the alcohol measuring device 100 automatically sets the times at which the user B shall give a breath sample. For example, the sentence and hence the implementation regulation 37 specify that the user B has to give a breath sample each twice a day at randomly selected times. The random generator of the alcohol measuring device 100 specifies two random sampling times again each day.

The alcohol measuring device 100 determines that a predefined or automatically, e.g., randomly set sampling time is reached and it then outputs, e.g., on the output unit 13, a prompt that the user B has to give now a breath sample, in one configuration such that the user B does not know the required time of sampling in advance.

The image recording device 12 generates at least one image 51 of the giving person P. The alcohol measuring device 100 preferably checks whether the person P is indeed giving a breath sample from himself or herself or introduces air into the input unit 3 in another manner. The alcohol measuring device 100 further determines the time ti at which this person P is giving the breath sample and preferably whether the testing device 1 or an input unit 3 is visible in the image 51 and whether the face of the giving person P is sufficiently illuminated. The additional identification device optionally detects an additional identifying feature of the giving person P, e.g., a fingerprint.

The testing unit 6 of the alcohol measuring device 100 tests the breath sample given. The testing unit 6 decides at least whether the alcohol content in the breath sample is below the predefined limit or not. In one configuration, the alcohol measuring device 100 outputs on the output unit 13 a message that indicates whether the alcohol content in this breath sample is above or below the predefined limit. In another configuration, the alcohol measuring device 100 does not output any message in order to make a subsequent manipulation more difficult for the registered user B.

The alcohol measuring device 100 generates each time after a breath sample was given a message ErgN and transmits this message ErgN to the central data processing unit 50. It is also possible that the central data processing unit 50 polls the alcohol measuring device 100 automatically and triggers the transmission of the message. This message ErgN comprises

- the device code 58 of the alcohol measuring device 100 that has generated this message ErgN,
- optionally the identification code ID of the user B,
- the image or each image 51, which was generated during this sampling and shall show the face of the giving person P,
- optionally the additional detected identifying feature,
- the result of the testing, which the testing unit 6 determined for this sample,
- optionally, when the user B was prompted to give a breath sample,
- the measured time ti at which the sample was given as a time stamp,
- optionally the geoposition at which the breath sample was given, and
- optionally measured operating parameters and/or ambient parameters of the alcohol measuring device 100, which will be explained below.

The released alcohol measuring device 100 repeatedly transmits during the use phase a message ErgN to the above-mentioned central data processing unit 50. In one configuration, the alcohol measuring device 100 uses for this purpose a transmission process, which the user B specified at the time of registration, and it correspondingly uses the wireless communication unit 14 or the wired communication unit 16 of the base station 2 or also a wireless communication unit 9 of the testing device 1.

In the example according to FIG. 6, the user B has grown a beard during the use phase. The image 51 shows the face of the user B with this beard, while the images 40, 40.1 generated and transmitted during the activation phase show the face of the user B without a beard.

The central data processing unit 50 analyzes the transmitted message. It determines the use data set 42 for the registered user B in the use data bank 41 on the basis of the device code 58 and optionally on the basis of the identification code ID. The central data processing unit 50 automatically compares the image 51 or each image 51 of the giving person P in the transmitted message ErgN with the images 40, 40.1 of the registered user B, which are comprised by the use data set 41 for the registered user B. At least some of these images 40, 40.1 were transmitted as part of the activation image set InB during the activation phase to the activation device 30 and were added to the activation data set 32 and then to the use data set 42 for the user B. It optionally compares the transmitted additional identifying feature of the giving person P with the additional identifying feature in the use data set 42.

The central data processing unit 50 decides by image comparison whether the breath sample, to which the message ErgN is related, was given indeed by the registered user B or by another person. Since the images 40, 40.1 in the use data set 42 show the registered user B from different viewing directions, an image 51 in the transmitted message ErgN usually has a sufficiently high degree of agreement with at least one image 40, 40.1 in this use data set 42, provided that the user B gave the sample correctly. Otherwise, this sample is not from the registered user B or was not given correctly.

In one configuration, an authorized person compares, at least if the central data processing unit 50 does not determine an agreement, the image 51 or each image 51 transmitted in the message ErgN with the stored images 40, 40.1 and enters the result of the comparison. The central data processing unit 50 generates now a comparison on the output unit 48.

A plurality of images 40, 40.1 stored in the use data set 42, which were preferably generated according to the instruction of the alcohol measuring device 100, are compared during the use phase with the image 51 in the transmitted message ErgN. These images 40, 40.1 show a human being with a higher resolution than does a reference image 35 in an official document, so that the comparison can often be carried out automatically with a sufficient reliability during the use phase.

The central data processing unit 50 compares the contents of the transmitted messages with the implementation regulation 37 in the sentence, which is comprised by the use data set 42 for the registered user B. It decides automatically whether the registered user B complies with these conditions, especially whether the user gives a breath sample personally at the predefined frequency and at the predefined times and whether the alcohol content in each breath sample is below the predefined limit, and/or it triggers the step that an authorized person checks whether the user B has complied with the condition or not. Especially when one of these conditions is not met, the central data processing unit 50 outputs a corresponding message.

In one configuration, the central data processing unit 50 of an authorized person presents the times at which a person P has to give a breath sample into the device 100, and for each sample given

- the result of the testing for alcohol,
- the result of the checking of whether this sample was indeed given by the user B or by someone else,
- optionally an image 51 of the face of the person P, which was generated by the image recording device 12 of the person P giving the sample while the user was giving this sample, and
- optionally the respective duration and/or the geoposition of the sampling.

The authorized person decides whether the user B has hitherto complied with the condition or not.

In the configurations just described, the central data processing unit 50 and, if needed, an authorized person in a center decides during the use phase by image comparison whether the user B has given a breath sample from himself or herself or whether an attempted manipulation occurred. This configuration avoids the need to equip the alcohol measuring device 100 with a corresponding image comparison unit.

In an alternative configuration, the alcohol measuring device 100 additionally comprises such an image comparison unit. The images 40, 40.1, which were generated during the activation phase and were transmitted to the activation device 30, are stored in a local image data memory 19 of the alcohol measuring device 100.

In one configuration, the use data set 42 for the user B in the central use data bank 41 and/or in the local image data memory 19 is completed after each successful identification of the user B by the images of the user B, taken at the time of this identification. This makes it possible to identify the user B automatically even if the user is gradually changing, for example, because of hair growth/loss of hair or due to growing a beard or to scars or because the user is now wearing eyeglasses/not wearing eyeglasses any longer.

The image comparison unit of the alcohol measuring device 100 compares the image or each image of the giving person with the stored images of the registered user B automatically during the use phase. The alcohol measuring device 100 likewise generates a message, which is transmitted to the central data processing unit 50. The central data processing unit 50 polls the alcohol measuring device 100 regularly in one configuration. This message likewise comprises the time of sampling and the result of the testing for alcohol, but not necessarily the image or an image of the giving person P, but it does comprise the result of the checking of whether the sample was indeed given by the user B. This reduces the necessary bandwidth during the data transmission and/or saves time during the data transmission.

In one configuration, the activation device 30 and, if needed, an authorized person compare the image 51 of the giving person P with the images 40, 40.1 of the user B, which are comprised in the use data set 42, during the use phase only if the image comparison unit of the alcohol measuring device 100 has not determined an agreement with sufficient certainty.

As was described already, the alcohol measuring device 100 repeatedly transmits during the use phase a message ErgN to the central data processing unit 50, this message ErgN comprising a device code 58,
the time t1, t2, . . . of a sampling,
the result of the analysis of this sampling,
in one configuration at least one image 51 of a person P, who is giving the sample, and
optionally an additional identifying feature of the giving person P. FIG. 6 shows as an example that the use data set 42 is completed by the results e1 and e2. These results e1 and e2 were obtained by the testing unit 6 at the times t1 and t2, respectively.

The transmitted messages ErgN are analyzed in order to decide from the distant location automatically and/or by an authorized person whether the user B has complied with the condition or each condition in the sentence or in the commitment or not. If the alcohol measuring device 100 is defective, it cannot be checked from the remote location whether the user B complies with the condition or commitment or not. A user B could therefore be tempted to put the alcohol measuring device 100 deliberately out of operation in order to consume alcohol in violation of the sentence or commitment without the violation of the condition or commitment being noticed, because, as a rule, a violation must be proven to the user B and the user B does not have to prove that the user has behaved correctly. The alcohol measuring device 100 may also become defective without this having been brought about by the user intentionally.

The system for monitoring the alcohol measuring device 100, which will be described below, reduces this risk of an undetected defect. This system can be used for an alcohol measuring device 100, which was activated as described, or for another alcohol measuring device, which is in the possession of the user B, for example, in their private sphere. The alcohol measuring device 100 likewise comprises an input unit 3, a testing unit 6 and an image recording device 12 as well as optionally further above-mentioned components.

The monitoring system may be a part of the alcohol measuring device 100 or may be located at a remote location in space from the alcohol measuring device 100 or contain parts that belong to the alcohol measuring device 100 and parts that are located at a distance in space from the alcohol measuring device 100, and belong, e.g., to an analysis system located at a distance in space.

A monitoring system, which is located at a distance in space and is consequently a separate monitoring system, is sent, for example, together with the alcohol measuring device 100 to the user B. In an alternative configuration, only the alcohol measuring device 100 is sent at first, and the monitoring system is sent then, when this alcohol measuring device 100 has been released for the user B, as was described above. It is also possible that the monitoring system is sent to the user B as a response to the fact that a defect or failure of the alcohol measuring device 100 was detected or is suspected.

Figure 7:
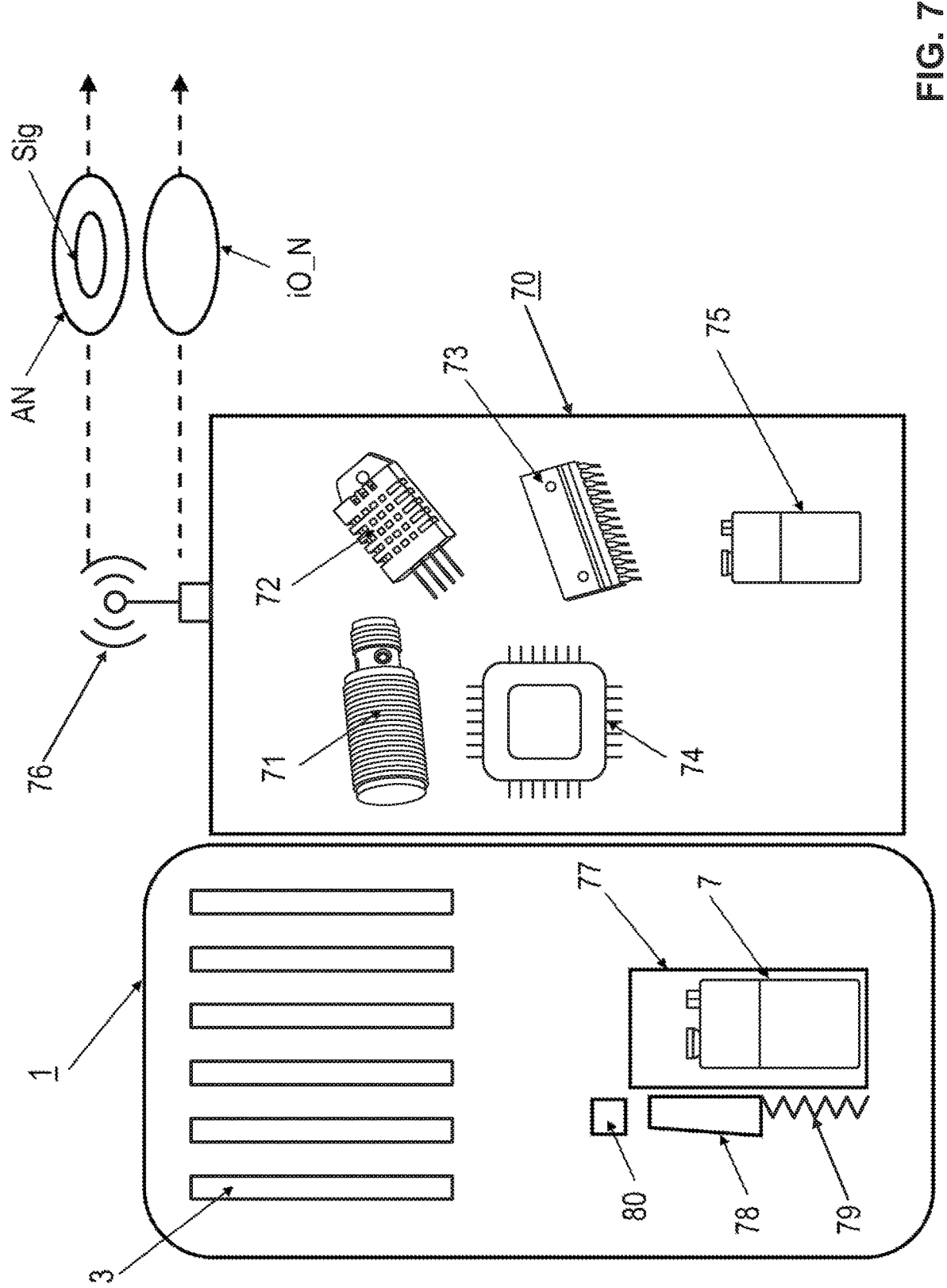
FIG. 7 is a schematic view showing the monitoring system for the alcohol measuring device.

FIG. 7 schematically shows such a monitoring system 70, which is permanently connected to the testing unit 1 in the example shown. The size of the monitoring system 70 is shown in an exaggerated form. To this monitoring system 70 belong at least one environmental sensor 71, 72,
a data-processing analysis unit 73,
a monitoring control device 74,
a separate power supply unit 75, and
a data transmission unit 76.

The monitoring system 70 is preferably accommodated in a housing offering protection against heat, moisture, harmful chemical effects and/or the effect of force. The data transmission unit may be identical to the above-described communication unit 9, 14 of the alcohol measuring device 100 or be a separate data transmission unit 76. The control device may be the control device 5, 15 of the alcohol measuring device 100 or a separate monitoring control device 74. The power supply unit may be the rechargeable power supply unit 7 of the alcohol measuring device 100 or a power supply unit 75 that is separate in space, which supplies exclusively the parts of the monitoring system 70. The environmental sensor 71, 72 or at least one environmental sensor 71, 72 or even each environmental sensor 71, 72 may be a part of the alcohol measuring device 100 or be located at a distance in space from the alcohol measuring device 100.

The environmental sensor 71, 72 or each environmental sensor 71, 72 of the monitoring system 70 is capable of measuring a respective ambient condition at which the alcohol measuring device 100 is used or could be used. For example, at least one environmental sensor 71, 72 is capable of measuring the following ambient conditions:

a temperature in the environment of the alcohol measuring device 100,
a change in this temperature over time,
a humidity in the environment of the alcohol measuring device 100,
a change in this humidity over time,
a force acting on the alcohol measuring device 100,
a change in this force over time, i.e., the acting acceleration,
an ambient pressure, which acts on the alcohol measuring device 100,
the effect of a harmful substance, e.g., an acid or
another chemical effect on the alcohol measuring device 100.

The analysis unit 73 automatically compares the ambient condition or each ambient condition that was measured by the environmental sensor 71, 72 or by a respective environmental sensor 71, 72, to a predefined limit or to another desired range for this ambient condition. In order for the alcohol measuring device 100 to be able to operate as desired, the ambient condition must be below a limit or generally in a predefined desired range. Each or at least one of the following attempted manipulations, which a user B (or another person) possibly makes, or one of the following unintentional actions or events can be detected by this comparison:

The user B puts the power supply unit 7 of the testing device 1 out of operation or fails to recharge this power supply unit 7.

The user B exposes the alcohol measuring device 100 to a high or rapidly rising temperature, for example, by placing into an oven or on a stove top or by throwing it into a fire.

The user B exposes the alcohol measuring device 100 to high humidity or to a rapidly rising humidity, for example, by the user B submerging the alcohol measuring device 100 in water or in another liquid.

The user B throws the alcohol measuring device against the wall or drops it on the floor.

The user pours an acid or gasoline or another harmful and/or combustible liquid over the alcohol measuring device 100.

The user B steps on the alcohol measuring device 100 or hits it, e.g., with a hammer, or the user places a heavy object on the alcohol measuring device 100 or drives over the alcohol measuring device 100 with an automobile.

If the analysis unit 73 detects the event that the ambient condition or at least one ambient condition is outside the desired range for that ambient condition, the control device 74 of the monitoring system 70 takes the following steps automatically and immediately:

The monitoring control device 74 generates a signal Sig, which characterizes the detected event.

The monitoring control device 74 prompts the data transmission unit 76 to transmit a message AN with this generated signal Sig to at least one predefined receiver located at a distance in space. This receiver is, for example, the central data processing unit 50 in a center, which monitors released alcohol measuring devices in the possession of users from a remote location.

In one configuration, the monitoring control device 74 prompts, in addition, the output unit of the alcohol measuring device 100 to output a message, which characterizes the detected event. The user B is informed thereby of the inadmissible ambient condition. The inadmissible ambient condition may also occur without the user B having intended it to happen.

The monitoring control device 74 of the monitoring system 70 prompts, in addition, the data transmission unit 76 to transmit a message iO_N to the receiver located at a distance in space at regular intervals, for example, every 12 or 24 hours, wherein this message iO_N indicates a trouble-free operation of the alcohol measuring device 100. If this message iO_N is not transmitted, it is possible, in particular, to detect the event that a user B fails to charge the rechargeable power supply unit 7, 18 of the alcohol measuring device 100 or has destroyed the alcohol measuring device 100, without the data transmission unit 14, 16 still having been able to send a message.

As was described above, the monitoring system 70 comprises a separate power supply unit 75 or uses, for example, a power supply unit 7 or 18 of the alcohol measuring device 100. A user B could attempt to put the alcohol measuring device 100 proper or the monitoring system 70 out of operation by removing these power supply units 7, 18, 75 from the monitoring system 70 or from the alcohol measuring device 100, so that neither the monitoring system 70 nor the alcohol measuring device 100 will function. The following configuration reduces the risk that the user B can do this undetected. A safeguard for the power supply unit 7 of the testing device 1 will be explained as an example.

A microswitch 78 (tamper switch) seals the housing 77, in which the power supply unit 7 of the testing device 1 is accommodated. This microswitch 78 comprises, for example, a beveled switch. This housing 77 is closed during the regular operation, and the beveled switch 78 is permanently pressed, e.g., against the force of a spring 79. If anyone attempts to open this housing 77, the microswitch 78 is also moved, e.g., by the force of the spring 79. A contact switch 80 detects the event that the housing 77 is opened, e.g., by the contact switch 80 detecting a movement or a certain position of the microswitch 78. In response to the detection of this event, the control device 74 generates a signal Sig, which characterizes the opening of the housing 77, and prompts the data transmission unit 76 to transmit an alarm message AN with this signal Sig to the receiver 50 located at a remote location in space. This process is carried out in many cases so rapidly that the alarm message AN is sent before the power supply unit 7 is removed from the housing 77 and the data transmission unit 76 possibly also ceases as a result to be supplied with electricity any longer.

In one configuration, the alcohol measuring device 100 comprises, furthermore, at least one mechanical sensor, which changes its state irreversibly when the alcohol measuring device 100 is exposed to an inadmissible ambient condition. The mechanical sensor makes it possible to detect at least one inadmissible ambient condition after the event and to prove it in court if needed. Examples of such mechanical sensors are:

A glass tube in the interior of the alcohol measuring device 100 or another element, which is more fragile than the rest of the alcohol measuring device 100, breaks if the alcohol measuring device 100 is subjected to an unacceptably strong force or acceleration or ambient pressure or other mechanical stress.

A first indicator paper changes its color at high humidity.

A second indicator paper changes its color at high temperature.

A third indicator paper changes its color under the influence of a certain substance, which is harmful for the alcohol measuring device 100.

While specific embodiments of the invention have been shown and described in detail to illustrate the application of the principles of the invention, it will be understood that the invention may be embodied otherwise without departing from such principles.

LIST OF REFERENCE CHARACTERS

1 Mobile testing device of the alcohol measuring device 100; it comprises the testing unit 6, the input unit 3, the power supply unit 7 in the housing 77, the contact points 8, the wireless communication unit 9, the control device 5 and the housing 4

2 Base station of the alcohol measuring device 100; it comprises the image recording device 12, the output unit 13, the wireless communication unit 14, the control device 15, the wired communication unit 16, the coupling point 17, the contact points 11, the power supply unit 18, the optional image data memory 19, the light source 20, the distance sensor 21 and the housing 10

3 Input unit of the testing device; it makes it possible for a person to give a breath sample 4 Housing of the testing device 1
5 Control device of the testing device 1
6 Testing unit of the base station 2; it tests the content of alcohol in a given breath sample
7 Power supply unit of the testing device 1; accommodated in the housing 77
8 Contact points of the testing device 1; with the testing device 1 inserted, they are in contact with the contact points 11 of the base station 2
9 Wireless communication unit of the testing device 1
10 Housing of the base station 2
11 Contact points of the base station 2; with the testing device 1 inserted, they are in contact with the contact points 8
12 Image recording device of the base station 2; it generates images of a person P, who uses the testing device 1 and gives a breath sample
13 Output unit of the base station 2; it outputs messages perceptible for a human being
14 Wireless communication unit of the base station 2
15 Control device of the base station 2
16 Wired communication unit of the base station 2
17 Coupling point of the base station 2; it connects the base station 2 to a stationary power supply grid
18 Power supply unit of the base station 2
19 Image data memory of the base station 2, in which images of a giving person are stored, wherein these images have been generated by the image recording device 12
20 Light source of the base station 2; it illuminates the area in front of the image recording device 12
21 Distance sensor of the base station 2; it measures the distance to an object located in front of the image recording device 12
30 Activation device; it comprises the central computer 33, the wired communication unit 34, the output unit 38 and the input unit 39; it has read access and write access to the activation data bank 31 at least at times
31 Activation data bank of the activation device 30; it comprises the activation data set 32 for the user
32 Activation data set for the user B in the activation data bank 31; it comprises the identification code ID, the reference image 35, the copy 36 of the sentence and the implementation regulation 37 and later the device code 58 as well as optionally an additional identifying feature of the user B
33 Central computer of the activation device 30
34 Wired communication unit of the activation device 30
35 Reference image of the user B; it belongs to the activation data set 32
36 Copy of the sentence of the user B
37 Computer-evaluable implementation regulation, which specifies when the user B must give a breath sample into the alcohol measuring device 100; it belongs to the activation data set 32 and to the use data set 42
38 Output unit of the activation device 30
39 Input unit of the activation device 30
40 Image that the image recording device 12 generates of a person P who gives a sample during the activation phase; it also shows a part of the alcohol measuring device 100
40.1 Additional image of the face of person P; it does not show the alcohol measuring device 100.
41 Use data bank, to which the central data processing unit 50 has read access and write access; it comprises the use data set 42
42 Use data set for the user B in the use data bank 41
43 Central computer of the central data processing unit 50
44 Wired communication unit of the central data processing unit 50
48 Output unit of the central data processing unit 50; it comprises a screen
49 Input unit of the central data processing unit 50; it comprises, e.g., a mouse
50 Central data processing unit used during the use phase; it comprises the output unit 48 and the input unit 49; it has read access and write access to the use data bank 41
51 Image of a person P who gives a breath sample; it is generated during the use phase
58 Device code of the alcohol measuring device 100
70 Monitoring system; it comprises the environmental sensors 71, 72, the analysis unit 73, the data transmission unit 76, the power supply unit 75, the monitoring control device 74, the microswitch 78, the spring 79 and the contact switch 80; is capable of generating an alarm message AN
71, 72 Environmental sensors of the monitoring system 70
73 Data-processing analysis unit of the monitoring system 70; it analyzes signals from the environmental sensors 71, 72
74 Separate monitoring control device of the monitoring system 70
75 Power supply unit of the monitoring system 70
76 Separate data transmission unit of the monitoring system 70
77 Housing for the power supply unit 7 of the testing unit 1
78 Microswitch; it locks the housing 77
79 Spring, which holds the microswitch 78 in a locked and sealing desired position
80 Contact switch, which detects the event that the microswitch 78 has been moved out of the desired position
100 Alcohol measuring device; it comprises the testing unit 1, the base station 2 and optionally the monitoring system 70; it has the device code 58; it is released for the user B
AN Alarm message, generated by the monitoring system 70 in case of an inadmissible ambient condition; comprises the signal Sig
B Registered user, who must use the alcohol measuring device 100 according to a condition
B.1, . . . , B.N Images of the activation image set InB
B.k1, . . . , B.kM Images of the checked activation image set InB_iO
Br.1, . . . , Br.p Predefined viewing directions, which shall occur in the images of the activation image set InB
E1? Decision: Has the message with the activation image set InB arrived and been authorized in time?
E2? Decision: Do all images of the checked activation image set InB_iO show the same person or different persons?
E3? Decision: Is image comparison to be performed automatically by the central computer 33 or manually by a person at the screen 38:
E4? Decision: Does at least one image show the face of the user B with sufficient certainty?
E5? Decision: Does the verified comparison image set VM_ver have a sufficient number of images?
E6? Decision: Do the images of the verified comparison image set VM_ver show the user B from a sufficient number of different viewing directions Br.1, . . . , Br.p and under a sufficient number of different light conditions L1, . . . , Lr?

ErgN Message generated during the use phase, which comprises the result of the testing of a breath sample and is transmitted by the alcohol measuring device 100 to the central data processing unit 50

Fg Release message with the release of the alcohol measuring device 100 for the user B G.1, . . . , G.n Groups of images, which show each the face of the same person G.i0 Group with the lowest degree of non-agreement NÜG(i0)

ID Identification code of the user B

InB Activation image set; it is transmitted from the base station 2 to the activation device 30; comprises the images 40 and 40.1

InB_iO Checked activation image set; it comprises exclusively images that show the face of a person P completely and with a sufficient image quality iO_N Message that the alcohol measuring device 100 is working correctly L.1, . . . , L.r Predefined different light conditions N_Fg Message that the alcohol measuring device 1200 is not released for the user B NÜG(i) Degree of non-agreement of group G.i with the reference images S1 Step: Receiving data on the registered user B S2 Step: Create activation data set 32 for the user B S3 Step: Receiving message with the activation image set InB S4 Step: Checking whether the message received in step S3 comprises a sufficient number of images and whether it is authorized S5 Step: Sort out from the activation image set InB the images that do not show the face of a person completely and with a sufficient quality; it yields the checked activation image set InB_iO S6 Step: Check whether all images of the checked activation image set InB_iO show the same person or different persons S7 Step: Set the checked activation image set InB_iO as the comparison image set VM S8 Step: Group images of the checked activation image set InB_iO S9 Step: Calculate a degree of non-agreement NÜG(i) for each group G.i S10 Step: Identify the group GA with the lowest degree of non-agreement NÜG(i0) and use it as a comparison image set VM S11 Step: Calculate a degree of agreement ÜG(i) for each group B.i S12 Step: Check whether the degree of agreement ÜG(i) is above the agreement limit S13 Step: Prompt the display of the image B.i and of a reference image 35 on the screen 38

S14 Step: Detect the input by a user

S15 Step: Decide on the basis of the user input whether the image B.i shows the face of the user B with sufficient certainty or not S16 Step: Check whether the verified comparison image set VM_ver comprises at least one image for each viewing direction Br.i (i=1, . . . , p) and for each light condition L.j (j=1, . . . , r_)

Sig Signal in the alarm message AN; it shows an inadmissible ambient condition, to which the alcohol measuring device 100 is exposed ÜG(i) Degree of agreement between image B.i of the comparison image set VM and the reference images 35

VM Comparison image set with images; it comprises exclusively images that show the face of the user B and that are compared with the reference images 35

VM_ver Verified comparison image set; it comprises exclusively images that show the face of the user B with sufficient certainty and which optionally show the testing device 1

What is claimed is:

1. A process for activating a drug measuring device for a user to be tested for drugs, process comprising:

providing the drug measuring device, wherein the drug measuring device comprises an input unit, by means of which a person gives a user sample into the drug measuring device, a testing unit configured to detect a result that a content of at least one predefined substance in a sample given into the drug measuring device is above a predefined limit, and an image recording device configured to take at least one picture of the person who is giving the user sample into the input unit;

providing an activation data bank;

providing a data-processing activation device, which has read access at least at times and write access at least at times to the activation data bank, wherein the activation data bank has an activation data set that is created for the user and the activation data set comprises a reference image set with at least one predefined reference image of the face of a user;

providing an activation phase comprising the activation device receiving an activation image set generated by the image recording device of a used drug measuring device comprising the drug measuring device or another drug measuring device with an image recording device, wherein the activation image set comprises at least one image, which the image recording device of the used drug measuring device has taken and a checking whether the received activation image set meets a predefined release criterion or not, wherein said checking comprises an image comparison between the reference image set for the user and at least one image of the activation image set received;

during the activation phase carrying out the image comparison automatically with the activation device or triggering the image comparison at a distant location in space from the activation device and at a distant location in space from the drug measuring device or carrying out the image comparison automatically with the activation device and also triggering the image comparison at a distant location in space from the activation device and at a distant location in space from the drug measuring device such that a result of the image comparison is detected, wherein the activation device carries out the image comparison such that the release criterion is met only if at least one image of the activation image set has been recognized as an image that shows the face of the user from the predefined reference image;

with the activation device releasing the drug measuring device for the user if the release criterion is met;

with the activation device completing the activation data set for the user with at least one image of the activation image set, which least one image of the activation image set has been recognized as showing the face of the user if the release criterion is met; and with the drug measuring device released for the user, using the drug measuring device during a use phase subsequent to the activation phase for carrying out at least one drug test with the use of at least one image comprised by the activation data set for the user.

2. A process in accordance with claim 1, wherein the activation device carries out the image comparison such that the release criterion is met only if all the images that have been recognized as originating from the face of the user are recognized as showing the face of the user with at least two predefined, different viewing directions relative to the image recording device and/or under at least two different light conditions.

3. A process in accordance with claim 1, wherein:
the activation device automatically checks whether all the images of the activation image set which show the face of a person show at least two different persons or only one person;
the activation device automatically divides the images of the activation image set into groups if the images as a whole show at least two different persons such that all images of one group show the same person and two images of different groups show two different persons;
the activation device automatically selects a group having images that show the face of the user or makes a determination that no group consists of images that show the face of the user; and
the activation device automatically carries out the image comparison such that the release criterion is met if the group containing the images that show the face of the user meets the release criterion.

4. A process in accordance with claim 1, wherein:
during the image comparison, the activation device triggers at least once a display of at least one image of the activation image set, which image was received from the drug measuring device, and at least one reference image of the reference image set on an output device; and
during the image comparison, the activation device detects an input of a user of the output device and the activation device decides depending on at least one detected input whether the release criterion is met or not.

5. A process in accordance with claim 1, wherein the activation device carries out the image comparison such that the release criterion is met only if at least one image of the activation image set has been recognized as an image that shows the face of the user, while the user is giving a sample into the input unit, wherein this image shows the input unit at least partially.

6. A process in accordance with claim 1, wherein:
the image recording device of the drug measuring device is used to generate the images of the activation image set;
the image recording device of the drug measuring device outputs the images in a form perceptible for a human being;
the image recording device of the drug measuring device comprises an input for a person; and
the image recording device of the drug measuring device triggers the transmission of the activation image set to the activation device in response to the input.

7. A process in accordance with claim 1, wherein:
the drug measuring device is handed over to the user or is made available to the user prior to the activation phase;
the release of the drug measuring device riggers a transmission of a message with the release to the drug measuring device; and in response to the reception of the release message, the drug measuring device brings itself or is brought into a state in which the drug measuring device can be used for carrying out a drug test.

8. A process in accordance with claim 1, wherein:
after the release of the drug measuring device for the user the use phase is carried out with the use of a data processing unit;
the data processing unit is used during the use phase and is located at a distant location in space from the drug measuring device;
the data processing unit has read access at least at times to a use data bank containing a use data set for the user;
the use data set in the use data bank comprises at least one image of the user;
at least two images of the use data set show the user of the drug measuring device from different viewing directions and/or under different light conditions;
the use data set in the use data bank is identical to the activation data set for the user in the activation data bank or was generated with the use of the activation data set;
the drug measuring device repeatedly makes possible a carrying out of a drug test during the use phase; and
each drug test always comprises the steps of a person giving a sample into the drug measuring device, the testing unit testing whether the content of the substance in the sample given is above the predefined limit or not, the image recording device of the drug measuring device released for the user generating at least one image of the person who has given the sample, the image of the person giving the sample being transmitted to the data processing unit,
the data processing unit comparing the image of the person giving the sample, which image was transmitted from the drug measuring device, with the at least one image comprised by the use data set of the user, automatically deciding, depending on the result of the comparison, whether the sample was given by the user for whom the drug measuring device is released or by another person, or triggering a decision to be made and entered, and detecting a result of the decision.

9. A process in accordance with claim 8, wherein:
the data processing unit has write access at least at times to the use data bank;
during the use phase, the data processing unit receives at least once at least one additional image, which the image recording device of the drug measuring device released for the user generated at the time of a drug test;
during the use phase, the data processing unit checks whether the additional image or at least one additional image received during the use phase meets a predefined additional criterion,
wherein the additional criterion is met only if the additional image has been recognized as an image that shows the face of the user; and
during the use phase, if the additional criterion is met, the data processing unit completes the use data set for the user in the use data bank by the additional image.

10. An activation device for activating a drug measuring device for a user to be tested for drugs, wherein the drug measuring device comprises an input unit by means of which a person gives a user sample into the drug measuring device, a testing unit configured to detect a result that a content of at least one predefined substance in the user sample given into the drug measuring device is above a predefined limit, and an image recording device configured to take at least one image of a person, who gives the user sample into the input unit, the activation device comprising:
  a data reception device having read access at least at times and write access at least at times to an activation data bank with an activation data set for a user, which comprises a reference image set with at least one predefined reference image, which shows a face of the user, wherein the data reception device is configured to receive an activation image set that comprises at least one image, which was taken by the image recording device of the drug measuring device or by an image recording device of another drug measuring device, wherein the activation device is further configured:
  to check whether the received activation image set meets a predefined release criterion;
  to carry out, at a time of the checking, an image comparison between the reference image set for the user and the received activation image set;
  to carry out the image comparison automatically and/or to trigger the image comparison to be carried out at a distant location in space from the activation device and at a distant location in space from the drug measuring device, and to detect a result of the image comparison;
  to carry out the image comparison such that the release criterion is met only if at least one image of the activation image set has been recognized as an image that shows the face of the user;
  if the release criterion is met, to release the drug measuring device for the user; and
  if the release criterion is met to complete the activation data set for the user with at least one image of the activation image set, which has been recognized as an image showing the face of the user, wherein the drug measuring device released for the user can be used in a subsequent use phase to carry out at least one drug test with the use of at least one image, which comprised by the activation data set for the user.

11. An activation device in accordance with claim 10, wherein:
  the activation device is a part of the drug measuring device; and
  the activation device is configured to transmit a message with a result of the carry out the image comparison as to whether the release criterion is met or not to a receiver located at a distant location in space.

12. An activation device in accordance with claim 10, wherein:
  the activation device is configured to transmit a message for indicating a release to the drug measuring device if the drug measuring device is released for the user; and
  the drug measuring device can be used for a drug test after the reception of the release message.

13. An activation device in accordance with claim 10 in combination with the activation data bank to provide an activation unit, wherein:
  an activation data set for the user is created in the activation data bank; and
  the activation data set for the user comprises a reference image set with at least one predefined reference image, which shows the face of the user.

14. An activation system comprising:
  an activation device comprising a data reception device having read access at least at times and write access at least at times to an activation data bank with an activation data set for a user, which comprises a reference image set with at least one predefined reference image, which shows a face of a user, wherein the data reception device is configured to receive an activation image set that comprises at least one image, which was taken by the image recording device of the drug measuring device or by an image recording device of another drug measuring device, wherein the activation device is further configured:
    to check whether the received activation image set meets a predefined release criterion;
    to carry out, at a time of the checking, an image comparison between the reference image set for the user and the received activation image set;
    to carry out the image comparison automatically and/or to trigger the image comparison to be carried out at a distant location in space from the activation device and at a distant location in space from the drug measuring device, and to detect a result of the image comparison;
    to carry out the image comparison such that the release criterion is met only if at least one image of the activation image set has been recognized as an image that shows the face of the user; and
    if the release criterion is met, to release the drug measuring device for the user;
    if the release criterion is met to complete the activation data set for the user with at least one image of the activation image set, which has been recognized as an image showing the face of the user, wherein the drug measuring device released for the user can be used in a subsequent use phase to carry out at least one drug test with the use of at least one image, which comprised by the activation data set for the user;
  a drug measuring device wherein the drug measuring device comprises:
    an input unit by means of which a person gives a user sample into the drug measuring device;
    a testing unit configured to detecting the result that the content of at least one predefined substance the user sample given into the drug measuring device is above a predefined limit; and
    an image recording device configured to take at least one image of the person who is giving the user sample into the input unit, wherein the drug measuring device is configured to transmit at least one image generated by the image recording device to the activation device and the activation device is configured to activate the drug measuring device.

* * * * *